United States Patent
Stupp et al.

(10) Patent No.: US 9,650,421 B2
(45) Date of Patent: May 16, 2017

(54) SELF-ASSEMBLED NANOSTRUCTURES

(75) Inventors: Samuel I. Stupp, Chicago, IL (US); Yves Ruff, Evanston, IL (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 302 days.

(21) Appl. No.: 14/342,245

(22) PCT Filed: Aug. 31, 2012

(86) PCT No.: PCT/US2012/053553
§ 371 (c)(1),
(2), (4) Date: Oct. 8, 2014

(87) PCT Pub. No.: WO2013/033658
PCT Pub. Date: Mar. 7, 2013

(65) Prior Publication Data
US 2015/0031127 A1    Jan. 29, 2015

Related U.S. Application Data

(60) Provisional application No. 61/530,863, filed on Sep. 2, 2011.

(51) Int. Cl.
*C07K 14/00* (2006.01)
*A61K 47/48* (2006.01)
*A61K 31/713* (2006.01)
*H01L 51/00* (2006.01)

(52) U.S. Cl.
CPC .......... *C07K 14/001* (2013.01); *A61K 31/713* (2013.01); *A61K 47/48215* (2013.01); *A61K 47/48246* (2013.01); *A61K 47/48323* (2013.01); *A61K 47/48769* (2013.01); *H01L 51/0093* (2013.01); *C07K 14/00* (2013.01); *C07K 2319/20* (2013.01); *C07K 2319/73* (2013.01)

(58) Field of Classification Search
None
See application file for complete search history.

(56) References Cited

U.S. PATENT DOCUMENTS

| | | | |
|---|---|---|---|
| 6,555,693 B2 | 4/2003 | Ge et al. | |
| 6,635,417 B1 | 10/2003 | Dervan et al. | |
| 6,716,866 B2 | 4/2004 | McMinn et al. | |
| 6,777,425 B2 | 8/2004 | Burli et al. | |
| 6,825,228 B2 | 11/2004 | Burli et al. | |
| 6,958,240 B1 | 10/2005 | Baird et al. | |
| 7,078,536 B2 | 7/2006 | Ge et al. | |
| 7,122,626 B2 | 10/2006 | Ge et al. | |
| 7,129,214 B2 | 10/2006 | Hu et al. | |
| 7,223,833 B1 | 5/2007 | Nielson et al. | |
| 7,265,129 B2 | 9/2007 | Jones et al. | |
| 7,301,037 B2 | 11/2007 | Ge et al. | |
| 7,329,765 B2 | 2/2008 | Burli et al. | |
| 7,348,427 B2 | 3/2008 | Burli et al. | |
| 7,498,349 B2 | 3/2009 | Burli et al. | |
| 7,498,405 B2 | 3/2009 | Ge et al. | |
| 7,642,245 B2 | 1/2010 | Hu et al. | |
| 7,700,765 B2 | 4/2010 | Khalaf et al. | |
| 2002/0151707 A1 | 10/2002 | Kindsvogel et al. | |

FOREIGN PATENT DOCUMENTS

| | | |
|---|---|---|
| EP | 1 072 679 | 1/2001 |
| WO | WO 97/12896 | 4/1997 |
| WO | WO 98/39352 | 9/1998 |
| WO | WO 99/14226 | 3/1999 |
| WO | WO 2013/033658 | 3/2013 |

OTHER PUBLICATIONS

Vandermeulen et al., "Structure and Dynamics of Self-Assembled Poly(ethylene glycol) Based Coiled-Coil Nano-Objects", ChemPhysChem, 2004, p. 488-494.*
Ruff et al., "Precision Templating with DNA of a Virus-like Particle with Peptide Nanostructures", JACS, 2013, pp. 6211-6219.*
Brookes et al., "Parsimonious Regularization using Genetic Algorithms Applied to the Analysis of Analytical Ultracentrifugation Experiments," Proceedings of the 9th annual conference on Genetic and evolutionary computation, 2007, 361-368.
Brookes et al., "A two-dimensional spectrum analysis for sedimentation velocity experiments of mixtures with heterogeneity in molecular weight and shape," Eur Biophys J, 2009, DOI 10.1007/s00249-009-0413-5, 10 pages.
Cook D., "Medicinal chemistry of antisense oligonucleotides—future opportunities," Anti-Cancer Drug Design 1991, 6, 585-607.
Cui et al., "Self-Assembly of Peptide Amphiphiles: From Molecules to Nanostructures to Biomaterials," Biopolymers, 2010, 94(1): 1-18.
de la Escosura et al., "Encapsulation of DNA-Templated Chromophore Assemblies within Virus Protein Nanotubes," Angew. Chem. Int. Ed. 49(31): 5335-5338 (2010).
Demeler et al., "Sedimentation velocity analysis of highly heterogeneous systems," Anal. Biochem., 2004, 335(2): 279-288.
Demeler and Brookes, "Monte Carlo analysis of sedimentation experiments," Colloid & Polymer Science, 2007, 286(2): 129-137.
Demeler et al., UltraScan A Comprehensive Data Analysis Software Package for Analytical Ultracentrifugation Experiments. Analytical Ultracentrifugation—Techniques and Methods. Royal Society of Chemistry: 2005.
Derouchey et al., "Decorated Rods: A "Bottom-Up" Self-Assembly of Monomolecular DNA Complexes," J. Phys. Chem. B, 2006, 110(10): 4548-4554.
Derouchey et al., "Monomolecular Assembly of siRNA and Poly-(ethylene glycol)—Peptide Copolymers," Biomacromolecules, 2008, 9(2): 724-732.
Fraenkel-Conrat et al., "Reconstitution of Active Tobacco Mosaic Virus From Its Inactive Protein and Nucleic Acid Components," Proceedings of the National Academy of Sciences of the United States of America, 1955, 41(10): 690-698.
Gratton et al., "The Effect of Particle Design on Cellular Internalization Pathways," Proc. Natl. Acad. Sci. U. S. A., 2008, 105(33): 11613-11618.
Iwaura et al., "Effects of oligoDNA template length and sequence on binary self-assembly of nucleotide bolaamphiphile," Org. Biomol. Chem., 2007, 5(21): 3450-3455.

(Continued)

*Primary Examiner* — Lianko Garyu
(74) *Attorney, Agent, or Firm* — Casimir Jones SC; David W. Staple

(57) ABSTRACT

The present disclosure is directed to the preparation of nanostructures by the encapsulation of a charged compound with individual self-assembled unit nano structures.

14 Claims, 10 Drawing Sheets

(56) References Cited

OTHER PUBLICATIONS

Janssen et al., "ssPNA templated assembly of oligo(p-phenylenevinylene)s,", Chem. Commun., 2010, 46(1): 109-111.
Johannes et al., Self-assembled Architectures from Glycoluril. Ind. Eng. Chem. Res., 2000, 39: 3419-3428.
Johnson et al., "Analysis of data from the analytical ultracentrifuge by nonlinear least-squares techniques," Biophys. J., 1981, 36(3): 575-588.
Katz S., "The Reversible Reaction of Sodium Thymonucleate and Mercuric Chloride," J. Am. Chem. Soc., 1951, 74:2238-2245.
Kelly et al., "A Molecular Vernier," Tetrahedron Lett., 1998, 39(22): 3675-3678.
Klug, "The Tobacco mosaic virus particle: structure and assembly," Philosophical Transactions: Biological Sciences, 1999, 354(1383): 531-535.
Kroschwitz, et al., The Concise Encyclopedia of Polymer Science and Engineering, pp. 858-859, J. I., ed. John Wiley & Sons, 1990.
Lee et al., "Viruses and virus-like protein assemblies—Chemically programmable nanoscale building blocks," Nano Research, 2009, 2(5): 349-364.
Li et al., "Reconstruction of the M13 Major Coat Protein and Its Transmembrane Peptide Segment on DNA Template," Biochemistry, 2007, 46 (29), 8579-8591.
Liu et al., "A seven-helix coiled coil," Proc. Natl. Acad. Sci. U. S. A., 2006, 103(42): 15457-15462.
Lo et al., "Self-assembly of three-dimensional DNA nanostructures and potential biological applications," Curr. Opin. Chem. Biol., 2010, 14(5): 597-607.
Lo et al., "Templated Synthesis of DNA Nanotubes with Controlled, Predetermined Lenghts," J. Am. Chem. Soc., 2010, 132(30): 10212-10214.
Maeda et al., "Tumor-Selective Delivery of Macromolecular Drugs via the EPR Effect: Background and Future Prospects," Bioconjugate Chem., 2010, 21(5): 797-802.
Minten et al., "CCMV capsid formation induced by a functional negatively charged polymer," Org. Biomol. Chem., 2009, 7(22): 4685-4688.
Nielsen et al., "Sequence-selective recognition of DNA by strand displacement with a thymine-substituted polyamide," Science, 1991, 254, 1497-1500.
Niemeyer et al. "Self-assembled nanostructures based on DNA: towards the development of nanobiotechnology," Current Opinion in Chemical Biology, 2000, 4: 609-618.
Osada et al., "Quantized folding of plasmid DNA condensed with block catiomer into characteristic rod structures promoting transgene efficacy," J. Am. Chem. Soc. 132(35): 12343-12348 2010.
Palmer et al., "Molecular Self-Assembly into One-Dimensional Nanostructures," Acc. Chem. Res., 2008, 41(12): 1674-1684.
Ruiz-Carretero et al., "DNA-templated assembly of dyes and extended π-conjugated systems," Chem. Commun., 2011, 47(15): 4340-7.
Sagar et al., "Self-assembled snrfactant nano-strflctures important in drug delivery: A review," Indian Journal of Experimental Biology, 2007, 45: 133-159.
Sambrook et al., Molecular Cloning: A Laboratory Manual 2nd ed. 1989, 36 pages.
Sanghvi, Y. S., "Heterocyclic Base Modification in Nucleic Acids and Their Applications in Antisense Coligonucleotides," Chapter 15, Antisense Research and Applications, CRC Press, 1993, pp. 273-288.
Stepto et al., "Dispersity in Polymer Science," Pure Appl. Chem., 2009, 81(2): 351-353.
Stupp et al., "Supramolecular Materials: Self-Organized Nanostructures," Science, 1997, 276(5311): 384-389.
Thomas C.A., "The Interaction of HgCl2 with Sodium Thymonucleate," J. Am. Chem. Soc., 76:6032 1954.
Tominaga et al., "Finite, Spherical Coordination Networks that Self-Organize from 36 Small Components," Angew. Chem. Int. Ed., 2004, 43(42): 5621-5625.
Wang et al., "Cylindrical block copolymer micelles and co-micelles of controlled length and architecture," Science, 2007, 317(5838): 644-647.
Wang et al., "Interaction of a Self-Assembling Peptide with Oligonucleotides: Complexation and Aggregation," Biophys. J., 2007, 93(7): 2477-2490.
Yamane et al., "On the Complexing of Desoxyribonucleic Acid (DNA) by Mercuric Ion," J. Am. Chem. Soc., 83:2599 1961.
Yoshizawa et al., "Functional Molecular Flasks: New Properties and Reactions within Discrete, Self-Assembled Hosts," Angew. Chem. Int. Ed., 2009, 48(19): 3418-3438.
Zhang et al., "An extremely stable and orthogonal DNA base pair with a simplified three-carbon backbone," J. Am. Chem. Soc., 2005, 127:74-75.
Zimmermann et al., "A Novel Silver(I)-Mediated DNA Base Pair," J. Am. Chem. Soc., 2002, 124:13684-13685.
Zon et al., "Phosphorothioate oligonucleotides," Eckstein (ed.) Oligonucleotides and Analogues, 1st Ed., Oxford University Press, New York, 1991, pp. 87-108.
International Search Report, International Patent Application No. PCT/US2012/053553, mailed Dec. 20, 2012, 2 pages.

\* cited by examiner

SELF-ASSEMBLED NANOSTRUCTURES

CROSS REFERENCE TO RELATED APPLICATIONS

This application claims the priority benefit under 35 U.S.C. §119(e) of U.S. Provisional Application No. 61/530,863, filed Sep. 2, 2011, the disclosure of which is incorporated herein by reference in its entirety.

STATEMENT OF GOVERNMENT INTEREST

This invention was made with government support under Grant Number DMR-1006713 awarded by the National Science Foundation (NSF) and Grant Number DE-FG02-00ER45810 awarded by the Department of Energy (DOE). The government has certain rights in the invention.

FIELD OF THE INVENTION

The present disclosure is directed to the preparation of nanostructures by the encapsulation of a charged compound with individual self-assembled unit nanostructures.

BACKGROUND OF THE INVENTION

During the last decade the development of various peptides amphiphiles [Cui et al., Peptide Science 94(1): 1-18 (2010)] and self-assembling molecules led to the preparation of nanostructures having different morphologies like one dimensional nanofibers, nanobelts, ribbons or helices [Palmer et al., Acc. Chem. Res. 41(12): 1674-1684 (2008)]. The growth and dimensions of these open one dimensional self-assembly often lack the control that can be found in closed systems like self-assembled nanocages [Tominaga et al., Angew. Chem. Int. Ed. 43(42): 5621-5625 (2004); Yoshizawa et al., Angew. Chem. Int. Ed. 48(19): 3418-3438 (2009)] or DNA based nanostructures [Lo et al., J. Am. Chem. Soc. 132(30): 10212-10214 (2010); Lo et al., Curr. Opin. Chem. Biol. 14(5): 597-607 (2010)].

Different approaches have been proposed to control the length of one-dimensional self-assembled objects. For example, one can control the supramolecular polymerization of monomers interacting with a template by hydrogen bonding by capping or a vernier approach [Ross Kelly et al., Tetrahedron Lett. 39(22): 3675-3678 (1998)]. Control of the nucleation and kinetics of growth have been particularly effective in the case of cylindrical micelles formed by crystalline block-copolymers [Wang et al., Science 317 (5838): 644-647 (2007)], however as this method is based on the control of a supramolecular living polymerization, the nanostructures prepared using this methodology are still relatively polydisperse.

In 2008, a more versatile templating approach was proposed for the preparation of monodisperse self-assembled nanostructures [Bull et al., J. Am. Chem. Soc. 130(9): 2742-2743 (2008)]. This strategy was inspired by the self-assembly of helicoidal filamentous viruses like the TMV which is formed by the directed self-assembly of proteins (capsomers) on a RNA template [Klug, Philosophical Transactions: Biological Sciences 354(1383): 531-535 (1999)]. This bioinspired strategy involved specific interactions between a dumbbell-shaped template and the self-assembling peptide amphiphile. In aqueous solution, coassembly was favored by hydrophobic collapse resulting in the formation of non-spherical core-shell supramolecular aggregates with controlled dimensions, whereas the peptide amphiphile forms micrometer long nanofibers.

SUMMARY OF THE INVENTION

In an effort to extend previous work to templates that would be easily accessible and potentially bioactive, the oligo(phenylene ethylene) template was replaced with nucleic acids. In particular, double stranded DNA can be prepared in high purity and perfect monodispersity over a wide range of sizes. In addition, the potential for filamentous nucleic acid complexes for gene and siRNA delivery are of high interest. DNA templated self-assembly [Ruiz-Carretero et al., Chem. Commun. 47(15): 4340-7 (2011)] has been successfully used for the ordering of nucleobase analogs onto single stranded DNA [Janssen et al., Chem. Commun. 46(1): 109-111 (2010)] as well as for the self-assembly of one-dimensional nanostructures with controllable helicity [Iwaura et al., Org. Biomol. Chem. 5(21): 3450-3455 (2007)]. In these examples the size of the nucleic acid template was small, and the resulting structures did not consist of a nucleic acid template that would be coated by ligands similar to the construction of a filamentous virus. This type of architecture was proposed by Ralder et al. for the complex formation between short nucleic acids and PEG-PEI copolymers [DeRouchey et al., J. Phys. Chem. B 110(10): 4548-4554 (2006); DeRouchey et al., Biomacromolecules 9(2): 724-732 (2008)]. Such PEGylated complexes were shown to be monomolecular, but their morphology remains unclear in absence of proper structural characterization. Furthermore, prior to the present disclosure, these structure failed to show enough stability and biological activity for the delivery of nucleic acids.

Accordingly, the present disclosure provides a peptide segment comprising a first domain, a second domain and a third domain, wherein: (a) the first domain comprises a moiety that has binding affinity for a charged compound, and is positioned at a first terminus of the second domain; (b) the second domain comprises an amino acid sequence with a coiled-coil structure and is positioned between the first domain and the third domain; and (c) the third domain comprises a water soluble polymer and is positioned at a second terminus of the second domain, wherein a plurality of peptide segments have the ability to self assemble to form a capsomer. In various embodiments, the charged compound is selected from the group consisting of a polyanion and a polycation. In some embodiments, the second domain comprises a "molecular segment" in place of the amino acid sequence, said molecular segment having the ability to aggregate with additional molecular segments to form a cluster of molecules with a coiled coil structure as described above.

In further embodiments, the charged compound is a polyanion and the moiety is selected from the group consisting of:

a) a polynucleotide sufficiently complementary to the anion to hybridize to the polyanion, wherein in certain embodiments the polynucleotide is selected from the group consisting of i) a polynucleotide which can intercalate into the polyanion and ii) a polynucleotide that can form a triple helix with the polyanion;

b) a cationic compound with sufficient charge to bind to the polyanion;

c) a polycation with sufficient charge to bind to the polyanion;

d) a polypeptide with sufficient charge to bind to the polyanion;

e) a polypeptide with binding specificity for the polyanion;

f) a small molecule with binding affinity for the polyanion;

g) a compound that has a binding affinity for the minor and/or major groove of DNA;

h) a combination thereof.

In additional embodiments, the charged compound is a polycation and the moiety is selected from the group consisting of:

a) a polynucleotide sufficiently complementary to the polycation to hybridize to the polycation, wherein in certain embodiments the polynucleotide is selected from the group consisting of i) a polynucleotide which can intercalate into the polycation and ii) a polynucleotide that can form a triple helix with the polycation;

b) an anionic compound with sufficient charge to bind to the polycation;

c) a polyanion with sufficient charge to bind to the polycation;

d) a polypeptide with sufficient charge to bind to the polycation;

e) a polypeptide with binding specificity for the polycation;

f) a small molecule with binding affinity for the polycation; and g) a combination thereof.

In some embodiments, the moiety is selected from the group consisting of spermine, oligoethyleneimine or polyethyleneimine and a cationic peptide. In further embodiments, the cationic peptide is a protamine or a histone. In still further embodiments, the cationic peptide comprises at least three lysine and/or arginine residues.

The disclosure further provides embodiments wherein the amino acid sequence is at least about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more residues long. In a specific embodiment, the amino acid sequence comprises the sequence REGVAKALRAVANALHYNASALEEVADALQKVKM (SEQ ID NO: 1).

In related embodiments, the amino acid sequence comprises a sequence that is 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, or 75% identical to SEQ ID NO: 1, and maintains the ability to form the coiled-coil structure.

It is additionally contemplated by the disclosure that, in some embodiments, the amino acid sequence comprises at least one non-naturally occurring amino acid.

In various embodiments, the water soluble polymer has an average molecular weight of at least about 2 kilodaltons, and in further embodiments the water soluble polymer has an average molecular weight of about 2 kilodaltons to about 100 kilodaltons. In further embodiments, the water soluble polymer has an average molecular weight of at least about 2 kilodaltons to at least about 10, 20, 30, 40 or 50 kilodaltons. In additional embodiments, the water soluble polymer has an average molecular weight of at least about 10 kilodaltons to at least about 50, 60, 70, 80, 90 or 100 kilodaltons, or at least about 20 kilodaltons to at least about 50, 60, 70, 80, 90 or 100 kilodaltons, or at least about 30 kilodaltons to at least about 50, 60, 70, 80, 90 or 100 kilodaltons, or at least about 40 kilodaltons to at least about 50, 60, 70, 80, 90 or 100 kilodaltons. In still further embodiments, the water soluble polymer has an average molecular weight of at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100 or more kilodaltons.

It is further contemplated by the disclosure that the water soluble polymer is, in various embodiments, selected from the group consisting of polyethylene glycol (PEG), copolymers of ethylene glycol/propylene glycol, carboxymethylcellulose, dextran, pullutan, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), dextran, HPMA, Fleximer, poly(N-isopropylacrylamide-co-acrylic acid) (poly(NIPAAm-AA)) and a combination thereof.

In further aspects, the disclosure also provides a capsomer comprising a plurality of peptide segments, each according to any of the embodiments disclosed herein, wherein the capsomer is formed by the self-assembly of the plurality of peptide segments, and wherein a plurality of capsomers have the ability to self assemble to form a nanostructure. In some embodiments, each capsomer comprises at least two peptide segments, at least three peptide segments, at least four peptide segments, at least five peptide segments, at least six peptide segments, at least seven peptide segments, at least eight peptide segments, at least nine peptide segments, at least ten peptide segments, or more than ten peptide segments.

In some embodiments, the disclosure provides a capsomer, wherein a) every protein segment in the capsomer has the same water soluble polymer as each other peptide segment in the capsomer;

b) at least two protein segments in the capsomer have different water soluble polymers;

c) every protein segment in the capsomer has the same moiety that binds the charged compound;

d) at least two protein segments in the capsomer have different moieties that bind the charged compound;

e) every protein segment in the capsomer has the same second domain;

f) at least two protein segments in the capsomer have different second domains; or g) a combination thereof.

In another aspect, the disclosure provides a nanostructure comprising a plurality of capsomers, each capsomer according to any of the capsomers disclosed herein, and further comprising a charged compound. In some embodiments, the nanostructure comprises at least two different charged compounds.

In some embodiments, each capsomer is identical, while in further embodiments, at least two capsomers are not identical.

In some embodiments, the charged compound is a nucleic acid, and in further embodiments, the nucleic acid is double stranded. In still further embodiments, the nucleic acid is a double stranded circular plasmid or vector, DNA, RNA, a synthetic polynucleotide, or a small interfering RNA (siRNA).

In embodiments in which the charged compound is a plasmid or vector, it is further contemplated that in some embodiments, the plasmid is double stranded, the plasmid is circular, the vector is linear or the vector is a viral polynucleotide.

It is also contemplated by the disclosure that in some embodiments, the nucleic acid comprises at least 5 nucleotides. In additional embodiments, the nucleic acid comprises between at least 5 nucleotides and at least 1 megabase, between at least 5 nucleotides and at least 5 kilobases, between at least 100 nucleotides and at least 1 kilobase or between at least 1 kilobase and at least 1 megabase.

In some embodiments, the charged compound is encapsulated by a plurality of capsomers.

In further embodiments, it is contemplated that the nanostructure disclosed herein has an electronic property. The electronic property, in various embodiments, is selected from the group consisting of semiconductivity, conductivity and electrochromism.

In some embodiments, the nanostructure is a monodisperse filamentous structure.

The disclosure also provides, in various embodiments, a nanostructure wherein:

a) the moiety in the first domain of the peptide segment is spermine;

b) the second domain comprises the amino acid sequence (SEQ ID NO: 1)
REGVAKALRAVANALHYNASALEEVADALQKVKM.

c) the water soluble polymer of the third domain is polyethylene glycol with a molecular weight of 5 kilodaltons, and d) the charged compound is DNA.

In further embodiments, the nanostructure is a molecular wire.

In one aspect, the disclosure provides a method of preparing a nanostructure comprising the step of: combining (i) a plurality of peptide (or molecular) segments, each according to any of the embodiments disclosed herein; and (ii) a charged compound under conditions sufficient to allow self-assembly of the plurality of peptide segments into capsomers and self-assembly of the capsomers into the nanostructure. In some embodiments of the methods disclosed herein, the charged compound is a nucleic acid, and in further embodiments the nucleic acid is double stranded. In still further embodiments, the nucleic acid is a double stranded circular plasmid or vector, DNA, RNA, a synthetic polynucleotide or a small interfering RNA.

In further embodiments of the methods of the disclosure, the nucleic acid comprises at least 5 nucleotides, while in other embodiments the nucleic acid comprises between at least 5 nucleotides and at least 1 megabase, between at least 5 nucleotides and at least 5 kilobases, between at least 100 nucleotides and at least 1 kilobase or between at least 1 kilobase and at least 1 megabase.

In still further embodiments of the methods disclosed herein, it is contemplated that each of the plurality of peptide segments comprises at least two peptide segments, at least three peptide segments, at least four peptide segments, at least five peptide segments, at least six peptide segments, at least seven peptide segments, at least eight peptide segments, at least nine peptide segments, at least ten peptide segments, or more than ten peptide segments.

In some embodiments of the methods, the charged material is encapsulated by the capsomers, and in further embodiments the nanostructure has an electronic property. The electronic property, in some embodiments, is selected from the group consisting of semiconductivity, conductivity and electrochromism.

Further embodiments of the methods include those wherein the nanostructure is a monodisperse filamentous structure.

Additional aspects of the disclosure include a nano structure produced by any of the methods described herein.

A further aspect of the disclosure provides a method of transfecting a cell comprising the step of contacting the cell with any one or more of the nanostructures disclosed herein. In some embodiments, the cell is transfected in vitro and in further embodiments the cell is transfected in vivo. In one embodiment, the cell is a cancer cell.

Yet another aspect of the disclosure provides a method of preparing a capsomer comprising the step of: combining a plurality of peptide segments as disclosed herein under conditions sufficient to allow self-assembly of the plurality of peptide segments into a capsomer.

A further aspect of the disclosure provides a method of preparing a nanostructure comprising the step of: combining a plurality of capsomers as disclosed herein under conditions sufficient to allow self-assembly of the plurality of capsomers into a nanostructure.

DETAILED DESCRIPTION OF THE INVENTION

Figure 1:
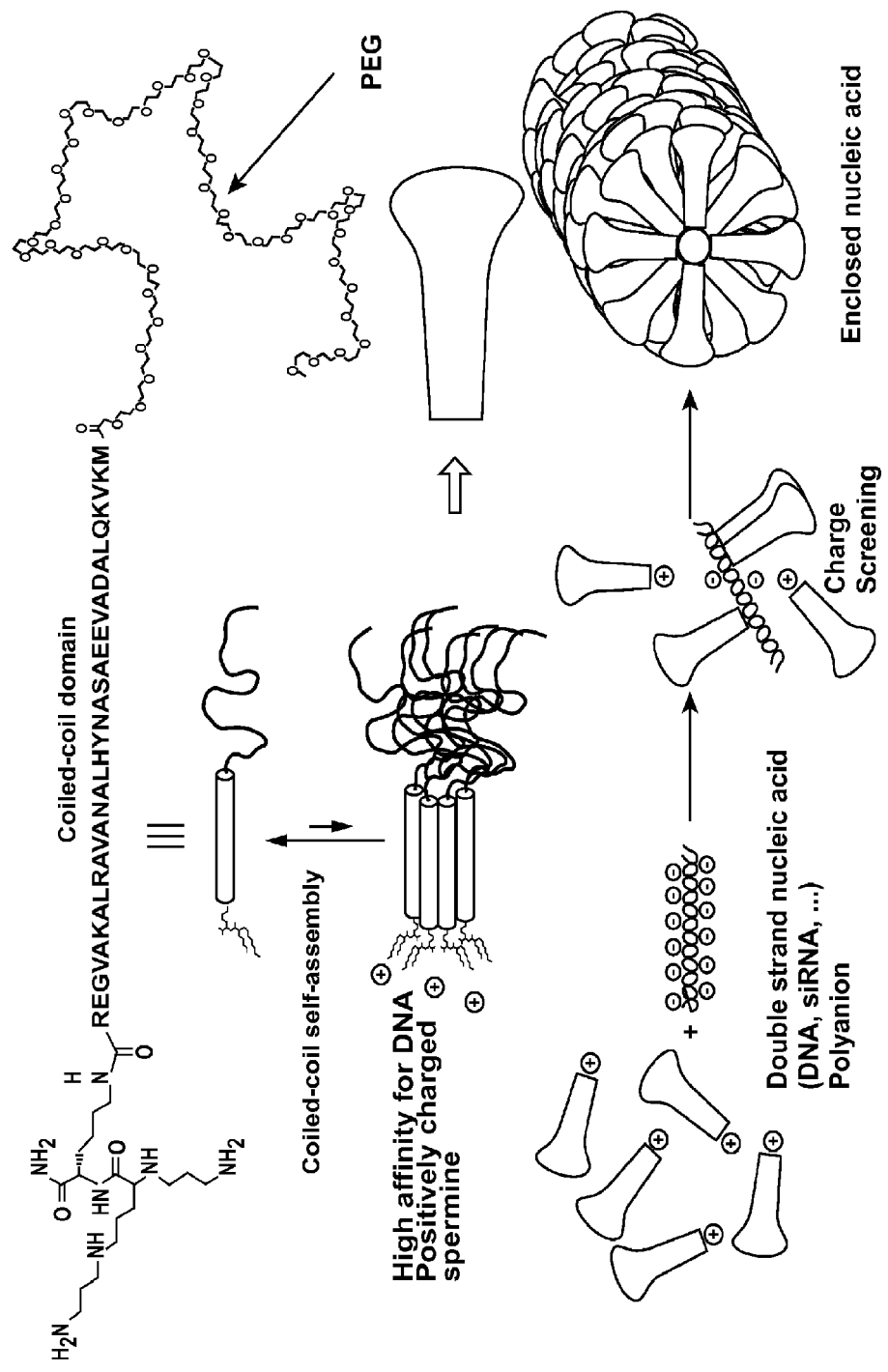
FIG. 1 depicts a schematic representation of the preparation of an exemplary synthetic filamentous viruses using a DNA template and self-assembled artificial capsomers created by the self-assembly of PEGylated coiled coil peptides (SEQ ID NO:1).

The present disclosure provides nanostructures that mimic the capsid proteins of natural filamentous viruses, and are useful for the delivery of charged compounds. The nanostructures comprise artificial self-assembled capsomers comprising coiled-coil peptides or molecular segments conjugated to a water soluble polymer. A threshold for the minimum molecular weight of the polymer segment was found to be crucial for the formation of monodisperse filamentous complexes. This result differentiates this disclosure from existing methodologies, which used non-self-assembling PEGylated block copolymers to complex DNA, as the previous approaches yielded mixtures of rods of different lengths as well as toroids. It is contemplated that the oligomerization of the individual rod-coil peptides or molecular segments, each as disclosed herein, and their aggregation on the template, results in the formation of a supramolecular star-brush architecture. For sufficiently long polymer segments, the steric repulsion between these branched polymer brushes results in an increased rigidity of the complexes. The stiffening of the filaments prevents their transition into unwanted architectures by counterbalancing the natural tendency of the neutralized charged compound core of the nanostructures to condense into toroids and buckle multiple times to form rods.

Compositions and methods disclosed herein demonstrate excellent control over both the morphology and dimensions of the complexes after optimization of the molecular design of the monomeric peptides, making this system advantageous for the preparation of highly homogenous one-dimensional nanostructures of defined length for the delivery of nucleic acids and other charged compounds.

It has previously been shown that the reconstitution of the active TMV viral particles can spontaneously occur in vitro just by mixing the viral RNA genome and the purified capsid proteins in aqueous solutions [Fraenkel-Conrat et al., Proceedings of the National Academy of Sciences of the United States of America 41(10): 690-698 (1955)]. The present disclosure describes methods to mimic this process by the use of completely synthetic capsomer analogs able to bind nucleic acids with high affinity and form a well-ordered artificial capsid around a nucleic acid template. Analogs of viral proteins have been produced by genetic engineering or chemical functionalization of the native protein to create functional virus that can be used as template themselves for the development of new materials or bioactive nanostructures [Lee et al., Nano Research 2(5): 349-364 (2009)]. Nucleic acids [de la Escosura et al., Angew. Chem. Int. Ed. 49(31): 5335-5338 (2010)] or other negatively charged polyelectrolytes [Minten et al., Org. Biomol. Chem. 7(22): 4685-4688 (2009)] have been used as a template to reconstitute viral-like structures from native capsomers, but control of the dimensions of the assemblies was only achieved in the case of reconstituted closed icosahedral capsids. These approaches are limited by the inclusion of derivatives of the natural infectious particles and have limitations in the kind of modifications that can be easily achieved on the natural protein. For example, and without limitation, native viral proteins can be recognized as pathogens and induce an immune response; in addition, the expression of native viral proteins by genetic engineering is limited by the set of 20 natural amino acids that are available in the host organism.

The viral capsid proteins (capsomers) of the Tobacco Mosaic Virus (TMV) consist of a 158 amino acid protein with a molecular weight of 17 kDa. The core of the capsomer is comprised of a rigid bundle of alpha-helical segments, connected at one end to a nucleic acid binding domain and flexible loops on the other. The overall shape of this protein is cylindrical with a length of 7 nm and a width of 2 nm [Klug, Philosophical Transactions: Biological Sciences 354(1383): 531-535 (1999)].

It is contemplated herein that the protein capsomers as found in TMV be replaced by a self-assembled non-centrosymmetric nanostructure like the nanoscale "mushrooms" formed by entropy-limited finite crystallization of tri-block copolymers described previously [Stupp et al., Science 276(5311): 384-389 (1997)]. The self-assembly of these rod-coil molecules into monodisperse aggregates was extensively characterized by transmission electron microscopy. As these rod-coil polymers were initially designed to be soluble in organic solvents, they are not compatible with the aqueous conditions required to solubilize the nucleic acid template. Biocompatibilty could also be an issue with the oligophenyl rigid segment disclosed in Stupp et al.

Thus, a new design for the precursor for an artificial capsomer had to take into account several requirements: 1) A flexible chain that can prevent the aggregation of the molecule and provide good solubility of the complex in water; 2) A biocompatible rigid rod-like segment to promote the aggregation of the monomeric rod-coil; and 3) The presence of a nucleic acid binding unit at one extremity of the molecule.

The monodisperse aggregates disclosed herein have a similar size and shape to viral capsid proteins, and in various embodiments they are also designed to expose selectively solubilizing groups or a DNA binding unit by attaching them at the extremity of the rod or the coil segment.

As used herein, "hybridization" means an interaction between two or three strands of nucleic acids by hydrogen bonds in accordance with the rules of Watson-Crick DNA complementarity, Hoogstein binding, or other sequence-specific binding known in the art. Hybridization can be performed under different stringency conditions known in the art.

As used herein, "sufficiently complementary" means to hybridize sufficiently well and with sufficient "binding specificity," to: (i) associate with a binding partner and/or (ii) give the desired disruption of the function of a target molecule. Similarly, "sufficient charge" is used herein to describe an amount of charge (i.e., a positive or negative charge) that allows two compounds described herein to associate with one another.

The term "monodisperse" as used herein refers to a plurality of nanostructures that have essentially the same size, shape, or mass, or refers to a single nanostructure composed of peptide segments of a uniform size and/or mass. In this context, the term "essentially" means that the plurality of nanostructures differs in size, shape or mass by about 10%-20% or less. Dispersity, represented by the symbol Đ and calculated using the equation: Đ $=M_m/M_n$, where $M_m$ is the mass-average molar mass and $M_n$ is the number-average molar mass [Stepto et al., Pure Appl. Chem. 81(2): 351-353 (2009)]. Methods of determining dispersity are known in the art and include, without limitation, gel permeation chromatography (also known as size exclusion chromatography), light scattering measurements such as dynamic light scattering, and/or direct calculation from matrix-assisted laser desorption/ionization (MALDI) or from electrospray mass spectrometry.

As used herein, the term "target" or "target polynucleotide" refers to a polynucleotide against which a given polynucleotide can be directed.

The term "small molecule," as used herein, refers to a chemical compound, for instance a peptidometic that may optionally be derivatized, or any other low molecular weight organic compound, either natural or synthetic. By "low molecular weight" is meant compounds having a molecular weight of about 1000 Daltons, typically between 300 and 700 Daltons. Low molecular weight compounds, in various aspects, are about 100, about 150, about 200, about 250, about 300, about 350, about 400, about 450, about 500, about 550, about 600, about 650, about 700, about 750, about 800, about 850, about 900 or about 1000 Daltons.

"Binding affinity," as used herein, means an ability of one binding partner to specifically associate with another. It is contemplated that binding affinity can be measured, for example by $K_D$, via assays known in the art.

It is noted here that, as used in this specification and the appended claims, the singular forms "a," "an," and "the" include plural reference unless the context clearly dictates otherwise.

It is also noted that the term "about" as used herein is understood to mean approximately.

General Design of Structures of the Disclosure

The structure described herein that is formed based on the three requirements described above (i.e., 1) a flexible chain that can prevent the aggregation of the structure and provide good solubility of the complex in water; 2) a biocompatible rigid rod-like segment to promote the aggregation of the monomeric rod-coil; and 3) the presence of a nucleic acid binding unit at one extremity of the molecule) is referred to herein as a "peptide segment." A plurality of peptide segments, when self-assembled, forms a capsomer as defined herein. Finally, a nanostructure as defined herein is formed via the self-assembly of a plurality of capsomers which encapsulate a charged compound. According to the disclosure, and in various aspects, the positively charged clusters of peptide (or molecular) segments which form a capsomer are effective at binding to a polynucleotide and creating a filament that has a uniform length equal to that of the polynucleotide.

Accordingly, in various aspects of the disclosure, a capsomer comprising a plurality of peptide segments is provided, wherein the capsomer is formed by the self-assembly of the plurality of peptide segments. A plurality of capsomers has the ability to self assemble to form a nanostructure. In some embodiments, each capsomer comprises at least two peptide segments, at least three peptide segments, at least four peptide segments, at least five peptide segments, at least six peptide segments, at least seven peptide segments, at least eight peptide segments, at least nine peptide segments, at least ten peptide segments, or more than ten peptide segments. In general, the upper and lower limit to the number of capsomers used to encapsulate a charged compound is determined by the negative charge density of the charged compounds (e.g., the nucleic acids), the number of positive charges of the capsomers, and the dimensions of both capsomers and charged compounds.

Design of the Self-Assembled Peptide Segments

Provided herein is a peptide segment comprising a first domain, a second domain and a third domain, wherein: (a) the first domain comprises a moiety that has binding affinity for a charged compound, and is positioned at a first terminus of the second domain; (b) the second domain comprises an amino acid sequence with a coiled-coil structure and is positioned between the first domain and the third domain; and (c) the third domain comprises a water soluble polymer and is positioned at a second terminus of the second domain, wherein a plurality of peptide segments have the ability to self assemble to form a capsomer. In some embodiments, the second domain comprises a "molecular segment" that has the ability to aggregate with additional molecular segments to form a coiled coil structure as described herein.

The second and third domains of the design were exemplified by using polyethylene glycol and peptide chains as the flexible coil and the rod segments, respectively. As discussed herein and will be understood by those of skill in the art, polymers other than polyethylene glycol are readily amenable to the design. The parallel self-assembly of rod-like peptides, in some aspects, is achieved by using coiled-coil helical peptides, exemplified with the heptameric GCN4pLAA peptide [SEQ ID NO: 1; Liu et al., Proc. Natl. Acad. Sci. U.S.A. 103(42): 15457-15462 (2006)]. This 34 amino acid peptide adopts an amphipathic alpha helix conformation in water. Again, the worker of ordinary skill in the art will readily appreciate that any peptide that adopts this secondary structure is amenable to the design. In addition, the worker of ordinary skill recognizes that the second domain can comprise any structure (e.g., a molecular segment) that has the ability to adopt an alpha helix conformation in water. The hydrophobic collapse of the helix results in the formation of a stable barrel like structure in which seven peptide chains are aligned parallel with each other. According to the crystal structure, the dimensions of this coiled-coil cylinder are 5 nm in length and 3 nm in width [Liu et al., Proc. Natl. Acad. Sci. U.S.A. 103(42): 15457-15462 (2006)].

The first domain of the design was implemented by the incorporation of an exemplary spermine group as the DNA binding unit, a physiological nucleic acid ligand with a binding constant in the micromolar range. Clustering of this DNA binding unit resulted in the formation of a high affinity DNA binding domain at one extremity of the mushroom nanostructure. The design contemplates a variety of variations on this first domain, as well as a variety of binding units that will interact with the first domain.

In addition to favored interactions with the template by a multivalent display of the DNA binding units, oligomerization of the monomeric peptide into discrete nanostructures limits uncontrolled aggregation of the peptide buildings blocks. An additional propensity of the peptides to aggregate on their own promotes the aggregation of the rod-coil monomer by peptide-peptide interactions (hydrophobic collapse or β-sheet formation). This would result in poor control of the dimensions of the complexes with the formation of heterogenous amorphous aggregates, as observed for self-assembling DNA binding peptides based on β-sheet formation [Wang et al., Biophys. J. 93(7): 2477-2490 (2007)] or derived from phage M13 capsid protein [Li et al., Biochemistry 46 (29), 8579-8591 (2007)].

The propensity of the monomeric DNA binding peptide to self-assemble prior to DNA complexation also ensures a denser coating of the nucleic acid template, as in principle only one binding event between one peptide subunit and the template would be enough to coat the DNA with seven peptides in a coiled-coil formation. FIG. 1 illustrates the design and self-assembly synthetic filamentous viruses using the artificial capsomer methodology disclosed herein.

Moiety

The first domain of the peptide segment comprises a moiety that has binding affinity for a charged compound, and is positioned at a first terminus of the second domain. Thus, a "moiety" as used herein is a compound that can bind to a charged compound.

In some embodiments, the charged compound is a polyanion and the moiety is selected from the group consisting of:
a) a polynucleotide sufficiently complementary to the anion to hybridize to the polyanion; i) a polynucleotide which can intercalate into the polyanion; ii) a polynucleotide that can form a triple helix with the polyanion;
b) a cationic compound with sufficient charge to bind to the polyanion;
c) a polycation with sufficient charge to bind to the polyanion;
d) a polypeptide with sufficient charge to bind to the polyanion;
e) a polypeptide with binding specificity for the polyanion;
f) a small molecule with binding affinity for the polyanion;
g) a compound that has a binding affinity for the minor and/or major groove of DNA; and
h) a combination thereof.

In some embodiments, the charged compound is a polycation and the moiety is selected from the group consisting of:
a) a polynucleotide sufficiently complementary to the polycation to hybridize to the polycation; i) a polynucleotide which can intercalate into the polycation; ii) a polynucleotide that can form a triple helix with the polycation;
b) an anionic compound with sufficient charge to bind to the polycation;
c) a polyanion with sufficient charge to bind to the polycation;
d) a polypeptide with sufficient charge to bind to the polycation;
e) a polypeptide with binding specificity for the polycation;
f) a small molecule with binding affinity for the polycation; and
g) a combination thereof.

In various embodiments of the disclosure, the moiety is selected from the group consisting of spermine, oligoethyleneimine, polyethyleneimine and a cationic peptide.

In some embodiments, the cationic peptide comprises at least three lysine and/or arginine residues. In further embodiments, the cationic peptide is a protamine or a histone.

Charged Compound

A peptide segment as disclosed herein comprises a charged compound, which in various embodiments is a polycation or a polyanion. The terms "polycation" and "polyanion" are understood in the art and generally refer to compounds that comprise either a plurality of positively charged ions (i.e., polycation) or compounds that comprise a plurality of negatively charged ions (i.e., "polyanion").

Polyanions contemplated by the disclosure include, without limitation:
a) a polynucleotide sufficiently complementary to the anion to hybridize to the polyanion; i) a polynucleotide which can intercalate into the polyanion; ii) a polynucleotide that can form a triple helix with the polyanion;
b) a cationic compound with sufficient charge to bind to the polyanion;
c) a polycation with sufficient charge to bind to the polyanion;
d) a polypeptide with sufficient charge to bind to the polyanion;
e) a polypeptide with binding specificity for the polyanion;
f) a small molecule with binding affinity for the polyanion;
g) a compound that has a binding affinity for the minor and/or major groove of DNA; and
h) a combination thereof.

Similarly, polycations contemplated by the disclosure include, without limitation:
a) a polynucleotide sufficiently complementary to the polycation to hybridize to the polycation; i) a polynucleotide which can intercalate into the polycation; ii) a polynucleotide that can form a triple helix with the polycation;
b) an anionic compound with sufficient charge to bind to the polycation;
c) a polyanion with sufficient charge to bind to the polycation;
d) a polypeptide with sufficient charge to bind to the polycation;
e) a polypeptide with binding specificity for the polycation;

f) a small molecule with binding affinity for the polycation; and g) a combination thereof.

Polynucleotides

A polynucleotide is an oligomer comprised of nucleotides. A polynucleotide may be comprised of DNA, RNA or a combination thereof. In addition, a polynucleotide may be either linear or circular. Thus, in various embodiments, a charged compound is a nucleic acid. In some embodiments, the nucleic acid is double stranded, and in further embodiments, the nucleic acid is a double stranded circular plasmid or vector, DNA, RNA, a synthetic polynucleotide, or a small interfering RNA (siRNA). In embodiments wherein the nucleic acid is a plasmid or vector, the plasmid is double stranded, the plasmid is circular, the vector is linear or the vector is a viral polynucleotide.

The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-($C_3$-$C_6$)-alkynyl-cytosine, 5-fluorouracil, 5-bromouracil, pseudoisocytosine, 2-hydroxy-5-methyl-4-tr-iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Polynucleotides may also include modified nucleobases. A "modified base" is understood in the art to be one that can pair with a natural base (e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2 (3H)-one), G-clamps such as a substituted phenoxazine cytidine (e.g. 9-(2-aminoethoxy)-H-pyrimido[5,4-b][1,4] benzox-azin-2(3H)-one), carbazole cytidine (2H-pyrimido [4,5-b]indol-2-one), pyridoindole cytidine (H-pyrido[3',2':4, 5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. No. 3,687,808, U.S. Pat. Nos. 4,845,205; 5,130,302; 5,134, 066; 5,175,273; 5,367,066; 5,432,272; 5,457,187; 5,459, 255; 5,484,908; 5,502,177; 5,525,711; 5,552,540; 5,587, 469; 5,594,121, 5,596,091; 5,614,617; 5,645,985; 5,830, 653; 5,763,588; 6,005,096; 5,750,692 and 5,681,941, the disclosures of which are incorporated herein by reference.

Modified polynucleotides are contemplated for use wherein both one or more sugar and/or one or more internucleotide linkage of the nucleotide units in the polynucleotide is replaced with "non-naturally occurring" groups. In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

Modified polynucleotides may also contain one or more substituted sugar groups. In one aspect, a modification of the sugar includes Locked Nucleic Acids (LNAs) in which the 2'-hydroxyl group is linked to the 3' or 4' carbon atom of the sugar ring, thereby forming a bicyclic sugar group. The linkage is in certain aspects a methylene (—$CH_2$—)n group bridging the 2' oxygen atom and the 4' carbon atom wherein n is 1 or 2. LNAs and preparation thereof are described in WO 98/39352 and WO 99/14226, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Polynucleotides contemplated herein may be either linear or circular, and range from about 5 nucleotides to about 1,000,000 nucleotides (i.e., 1 megabase) in length. In some embodiments, the polynucleotide is between at least 5 nucleotides and at least 5 kilobases, between at least 100 nucleotides and at least 1 kilobase or between at least 1 kilobase and at least 1 megabase.

In further embodiments, a polynucleotide contemplated by the disclosure is about 5 to about 150, 300, 600, 1200 or more nucleotides in length, about 5 to about 90 nucleotides in length, about 5 to about 80 nucleotides in length, about 5 to about 70 nucleotides in length, about 5 to about 60 nucleotides in length, about 5 to about 50 nucleotides in length about 5 to about 45 nucleotides in length, about 5 to about 40 nucleotides in length, about 5 to about 35 nucleotides in length, about 5 to about 30 nucleotides in length, about 5 to about 25 nucleotides in length, about 5 to about 20 nucleotides in length, about 5 to about 15 nucleotides in length, about 5 to about 10 nucleotides in length, about 400 to about 10,000 nucleotides or more in length, and all polynucleotides intermediate in length of the sizes specifically disclosed to the extent that the polynucleotide is able to achieve the desired result. Accordingly, polynucleotides of 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more nucleotides in length are contemplated.

Polynucleotides contemplated for use according to the methods of the disclosure include those which modulate expression of a gene product expressed from a target polynucleotide. Accordingly, RNA polynucleotides which hybridize to a target polynucleotide and initiate an RNAse activity (for example RNAse H), triple helix forming polynucleotides which hybridize to double-stranded polynucleotides and inhibit transcription, and ribozymes which hybridize to a target polynucleotide and inhibit translation, are contemplated. Additional RNA polynucleotides contemplated by the disclosure include without limitation microRNA (miRNA), small interfering RNA (siRNA), premiRNA and small hairpin RNA (shRNA).

In one aspect, a plurality of nanostructures are provided that comprise identical polynucleotides, i.e., each polynucleotide has the same length and the same sequence. In other aspects, the plurality of nanostructures collectively comprise two or more polynucleotides which are not identical, i.e., at least one of the polynucleotides present in a nanostructure differs from at least one other polynucleotide present in a different nanostructure, in that it has a different length and/or a different sequence. In aspects wherein different polynucleotides are present in separate nanostructures, these different polynucleotides bind to the same single target polynucleotide but at different locations, or bind to different target polynucleotides which encode different gene products. Accordingly, in various aspects, a single composition comprising a plurality of nanostructures target more than one gene product. Polynucleotides are thus target-specific polynucleotides, whether at one or more specific regions in the target polynucleotide, or over the entire length of the target polynucleotide as the need may be to effect a desired level of inhibition of gene expression.

Methods for inhibiting gene product expression provided include those wherein expression of the target gene product is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 96%, at least about 97%, at least about 98%, at least about 99%, or 100% compared to gene product expression in the absence of a composition comprising a nanostructure as disclosed herein. In other words, methods provided embrace those which results in essentially any degree of inhibition of expression of a target gene product.

The degree of inhibition is determined in vivo from a body fluid sample or from a biopsy sample or by imaging techniques well known in the art. Alternatively, the degree of inhibition is determined in a cell culture assay, generally as a predictable measure of a degree of inhibition that can be expected in vivo resulting from use of a specific type of nanostructure comprising a specific polynucleotide.

Polypeptides

As used herein a "polypeptide" refers to a polymer comprised of amino acid residues. In some aspects of the disclosure, a nanostructure comprises a polypeptide as described herein. Polypeptides are understood in the art and include without limitation an antibody, an enzyme, a structural polypeptide and a hormone. In related aspects, the nanostructure comprising a polypeptide recognizes and associates with a target molecule and enables detection of the target molecule.

Polypeptides of the present disclosure may be either naturally occurring or non-naturally occurring.

Naturally Occurring Polypeptides

Naturally occurring polypeptides include without limitation biologically active polypeptides (including antibodies) that exist in nature or can be produced in a form that is found in nature by, for example, chemical synthesis or recombinant expression techniques. Naturally occurring polypeptides also include lipoproteins and post-translationally modified proteins, such as, for example and without limitation, glycosylated proteins.

Antibodies contemplated for use in the methods and compositions of the present disclosure include without limitation antibodies that recognize and associate with a target molecule either in vivo or in vitro.

Structural polypeptides contemplated by the disclosure include without limitation actin, tubulin, collagen, elastin, myosin, kinesin and dynein.

Non-Naturally Occurring Polypeptides

Non-naturally occurring polypeptides contemplated by the present disclosure include but are not limited to synthetic polypeptides, as well as fragments, analogs and variants of naturally occurring or non-naturally occurring polypeptides as defined herein. Non-naturally occurring polypeptides also include proteins or protein substances that have D-amino acids, modified, derivatized, or non-naturally occurring amino acids in the D- or L-configuration and/or peptidomimetic units as part of their structure. The term "protein" typically refers to large polypeptides. The term "peptide" typically refers to short polypeptides (i.e., peptides typically comprise at least 2 and about 50 or fewer monomer units).

Non-naturally occurring polypeptides are prepared, for example, using an automated polypeptide synthesizer or, alternatively, using recombinant expression techniques using a modified polynucleotide which encodes the desired polypeptide.

As used herein a "fragment" of a polypeptide is meant to refer to any portion of a polypeptide or protein smaller than the full-length polypeptide or protein expression product.

As used herein an "analog" refers to any of two or more polypeptides substantially similar in structure and having the same biological activity, but can have varying degrees of activity, to either the entire molecule, or to a fragment thereof. Analogs differ in the composition of their amino acid sequences based on one or more mutations involving substitution, deletion, insertion and/or addition of one or more amino acids for other amino acids. Substitutions can be conservative or non-conservative based on the physicochemical or functional relatedness of the amino acid that is being replaced and the amino acid replacing it.

As used herein a "variant" refers to a polypeptide, protein or analog thereof that is modified to comprise additional chemical groups not normally a part of the molecule. Such groups may modulate, for example and without limitation, the molecule's solubility, absorption, and/or biological half-life. Groups capable of mediating such effects are disclosed in Remington's Pharmaceutical Sciences (1980). Procedures for coupling such groups to a molecule are well known in the art. In various aspects, polypeptides are modified by glycosylation, pegylation, and/or polysialylation.

Fusion proteins, including fusion proteins wherein one fusion component is a fragment or a mimetic, are also contemplated. A "mimetic" as used herein means a peptide or protein having a biological activity that is comparable to the protein of which it is a mimetic. By way of non-limiting example, an endothelial growth factor mimetic is a peptide or protein that has a biological activity comparable to the native endothelial growth factor. The term further includes peptides or proteins that indirectly mimic the activity of a protein of interest, such as by potentiating the effects of the natural ligand of the protein of interest.

This group of biomolecules includes antibodies along with fragments and derivatives thereof, including but not limited to Fab' fragments, F(ab)2 fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

Compound that has a Binding Affinity for the Minor and/or Major Groove of DNA

As described herein, a compound that has a binding affinity for the minor and/or major groove of DNA may also serve as the moiety that has a binding affinity for a charged compound. In various embodiments, the compound that has a binding affinity for the minor and/or major groove of DNA is selected from the group consisting of a heterocyclic peptide capable of binding the minor and/or major grooves of DNA, a polyamide that binds to specific nucleotide sequences in a minor groove of double stranded DNA (e.g., a 3-hydroxy-N-methylpyrrole/N-methylpyrrole carboxamide pair, a N-methylpyrrole/3-hydroxy-N-methylpyrrole pair, a N-methylimidizole/N-methylpyrrole carboxamide pair or a N-methylpyrrole/N-methylimidizole carboxamide pair), an aryl-benzimidazole compound, an isoquinoline compound, a benzothiophene compound, a halogen-substituted thienyl compound, a benzamide compound, a compound having a (pyrrole carboxamide)-(benzamide)-(imidazole carboxamide) motif, a biaryl compound, an oligopeptide compound comprising: (a) at least one nitrogen-containing basic group attached to at least one end of the oligopeptide; and (b) two or more heterocyclic monomers, at least one of which is substituted in the heterocyclic part by a branched, cyclic or part cyclic $C_{3-5}$ alkyl group, or a pharmaceutically acceptable salt or solvate thereof, or a combination of any of the foregoing; each as described in any of U.S. Pat. Nos. 5,698,674, 5,998,140, 6,303,312, 6,472,537, 6,555,693, 6,635,417, 6,716,866, 6,777,425, 6,825,228, 6,958,240, 7,078,536, 7,122,626, 7,129,214, 7,265,129, 7,301,037, 7,329,765, 7,348,427, 7,498,349, 7,498,405, 7,642,245 and 7,700,765, each of which is incorporated by reference herein in its entirety.

Water Soluble Polymer

As described herein, the third domain of the peptide segment comprises a water soluble polymer and is positioned at a second terminus of the second domain. In one embodiment, the water soluble polymer has an average molecular weight of at least about 2 kilodaltons.

In further embodiments, the water soluble polymer has an average molecular weight of about 2 kilodaltons to about 100 kilodaltons, or from about 2 kilodaltons to about 5, 10, 20, 50, 70 or 90 kilodaltons, or from about 5 kilodaltons to about 10, 20, 30, 40, 50, 60, 70, 80, 90 or 100 kilodaltons, or from about 10 kilodaltons to about 20, 50, 70, 90 or 100 kilodaltons, or from about 20 kilodaltons to about 50, 70, 90 or 100 kilodaltons, or from about 30 kilodaltons to about 50, 70 or 100 kilodaltons, or from about 50 kilodaltons to about 60, 70, 80, 90 or 100 kilodaltons. Accordingly, it is contemplated by the disclosure that, in various embodiments, the water soluble polymer has an average molecular weight of at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50, at least about 51, at least about 52, at least about 53, at least about 54, at least about 55, at least about 56, at least about 57, at least about 58, at least about 59, at least about 60, at least about 61, at least about 62, at least about 63, at least about 64, at least about 65, at least about 66, at least about 67, at least about 68, at least about 69, at least about 70, at least about 71, at least about 72, at least about 73, at least about 74, at least about 75, at least about 76, at least about 77, at least about 78, at least about 79, at least about 80, at least about 81, at least about 82, at least about 83, at least about 84, at least about 85, at least about 86, at least about 87, at least about 88, at least about 89, at least about 90, at least about 91, at least about 92, at least about 93, at least about 94, at least about 95, at least about 96, at least about 97, at least about 98, at least about 99, at least about 100 or more kilodaltons.

Water soluble polymers for use in the products and methods described herein are known to those of skill in the art. By way of non-limiting example, the water soluble polymer is selected from the group consisting of polyethylene glycol (PEG), copolymers of ethylene glycol/propylene glycol, carboxymethylcellulose, dextran, pullutan, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), monomethoxy-polyethylene glycol, dextran, poly-(N-vinyl pyrrolidone), propylene glycol homopolymers, a polypropylene oxide/ethylene oxide co-polymer, polyoxyethylated polyols (e.g., glycerol), dextran, HPMA, Fleximer, poly(N-isopropylacrylamide-co-acrylic acid) (poly(NIPAAm-AA)) and a combination thereof.

Nanostructure

As described herein, a nanostructure is formed via the self-assembly of a plurality of capsomers that encapsulate a charged compound. In some aspects, the nanostructure is a monodisperse filamentous structure.

In some aspects, the nanostructure possesses an electronic property. In various embodiments, the electronic property is selected from the group consisting of semiconductivity, conductivity and electrochromism, these properties being useful for the construction of electronic devices such as transistors or logic gates at the nanoscale. In another embodiment, the nanostructure is a molecular wire that is used to design and construct electronic circuits on the nanoscale.

In one specific embodiment of the disclosure, the nanostructure is a structure wherein:
a) the moiety in the first domain of the peptide segment is spermine;
b) the second domain comprises the amino acid sequence (SEQ ID NO: 1)
REGVAKALRAVANALHYNASALEEVADALQKVKM;

c) the water soluble polymer of the third domain is polyethylene glycol with a molecular weight of 5 kilodaltons, and
d) the charged compound is DNA.

In further embodiments, the disclosure provides a method of preparing a nanostructure comprising the step of: combining (i) a plurality of peptide segments, each according to any of the embodiments disclosed herein; and (ii) a charged compound under conditions sufficient to allow self-assembly of the plurality of peptide segments into capsomers and self-assembly of the capsomers into the nanostructure. Thus, in various aspects of the disclosure, the charged material is encapsulated by the capsomers.

In one embodiment, the charged compound is a nucleic acid, and in further embodiments the nucleic acid is double stranded. Additional embodiments of the disclosure provide a nucleic acid that is a double stranded circular plasmid or vector, DNA, RNA, a synthetic polynucleotide or a small interfering RNA.

Methods

In one aspect, the disclosure provides a method of transfecting a cell comprising the step of contacting the cell with a nanostructure of the disclosure. In various embodiments, the cell is transfected in vitro or the cell is transfected in vivo. In one embodiment, the cell is a cancer cell.

Accordingly, the disclosure provides methods of administering a composition comprising a nanostructure as described herein, comprising administering a therapeutically effective amount of the composition to a patient in need thereof. In related embodiments, a composition of the disclosure is co-administered with a second therapeutic agent, also in a therapeutically effective amount. In various aspects, the composition comprises a plurality of nanostructures, each comprising a different charged compound. In further aspects, at least two of the nanostructures in the plurality comprise the same charged compound.

In another aspect of the disclosure, a method of preparing a capsomer is provided comprising the step of: combining a plurality of peptide segments, each according to any of the peptide segments described herein, under conditions sufficient to allow self-assembly of the plurality of peptide segments into a capsomer.

A further aspect of the disclosure provides a method of preparing a nanostructure comprising the step of: combining a plurality of capsomers, each according to any of the capsomers described herein, under conditions sufficient to allow self-assembly of the plurality of capsomers into a nanostructure.

The disclosure further contemplates, in various aspects, the use of the nanostructures disclosed herein for:

Non-viral artificial nucleic acid vectors for in vitro cell transfection.

Non-viral artificial nucleic acid vectors for in vivo gene delivery.

Non-viral artificial nucleic acid vectors for in vivo siRNA delivery.

Cancer therapies using targeted non-viral artificial nucleic acid vectors for in vivo anti-metastatic or pro-apoptotic gene delivery to tumors.

Preparation of monodisperse virus like one-dimensional nanostructures with electronic properties.

While particular embodiments of the present disclosure have been illustrated and described, it would be obvious to those skilled in the art that various other changes and modifications can be made without departing from the spirit and scope of the disclosure. It is therefore intended to cover all such changes and modifications that are within the scope of this disclosure.

EXAMPLES

Example 1

Molecular Structure of Exemplary Self Assembling DNA Binding Peptides

Figure 2:
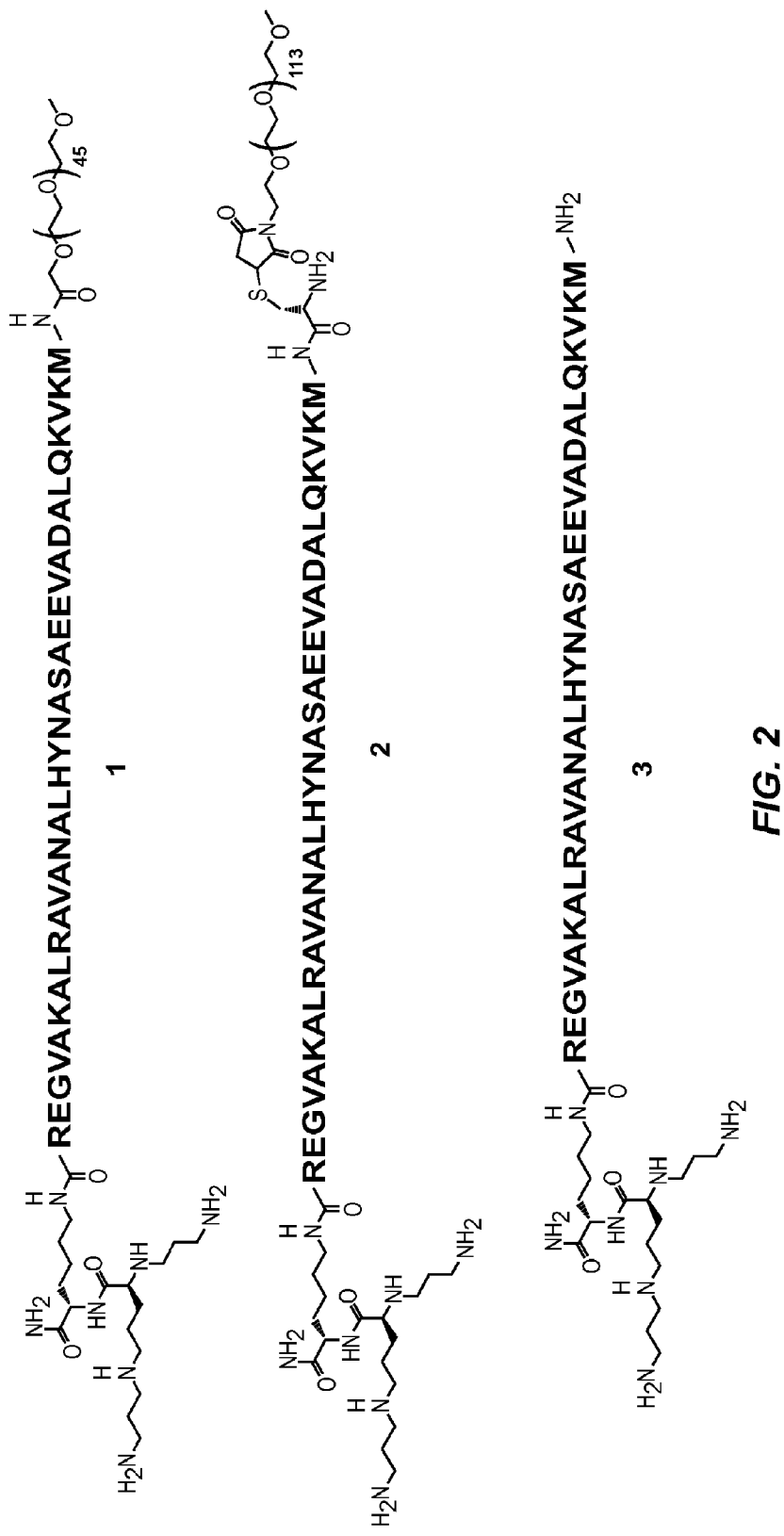
FIG. 2 shows molecular structures of the DNA binding coiled coil peptides (SEQ ID NO: 1) exemplified herein.

The design described herein above led to the synthesis of the following PEGylated DNA binding peptides (FIG. 2).

Synthesis of Peptide Segment

The synthesis of the peptidic segment was achieved by conventional solid phase synthesis on Tentagel-R-RAM resin using the Fmoc protecting group strategy. The introduction of the spermine DNA binding unit at the C-terminus of the coiled-coil peptide was achieved by coupling the Boc protected 5-carboxyspermine to the ϵ-amine of a lysine residue. The PEG chain was introduced by direct coupling of a $PEG_{2000}$ carboxylic acid to the free N-terminus of the peptide on solid phase to give 1, or by the conjugation of a commercial mPEG5000-maleimide to the coiled-coil peptide functionalize with a N-terminal cysteine residue to give 2. The individual monodisperse double strand NoLimits DNA fragments were purchased from Fermentas. The plasmid DNA templates were purchased from New England Biolabs.

Characterization of the Artificial Capsomers

Figure 3:
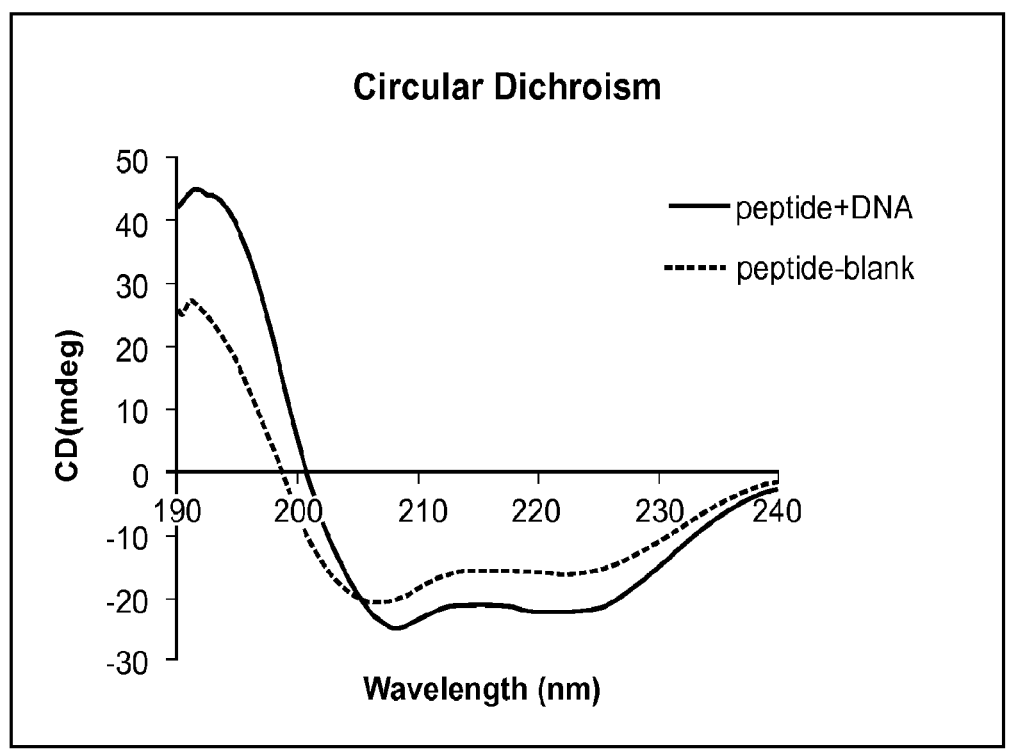
FIG. 3 depicts circular dichroism of peptide 1 at 21 µM at pH 8 in Tris buffer.

The self-assembly of molecules 1 and 2 into mushroom-shaped nanostructures by coiled-coil formation is an aspect of the disclosure. The self-assembly of the block copolymer 1 was characterized under physiological conditions to probe its propensity to generate heptameric coiled-coils aggregates. Circular dichroism demonstrated the alpha-helical nature of compounds 1. Interestingly, the alpha-helical content of the molecules increases from 36 to 53% both upon addition of DNA, suggesting a stabilization of the coiled-coil aggregates by screening of the cationic charges of the spermine units by interaction with DNA (FIG. 3).

Example 2

Sedimentation Analysis

Equilibrium:

The coiled-coil formation was then investigated further by analytical ultracentrifugation, which gives access to the absolute molecular weight of the aggregates in solution and subsequently their aggregation number. Equilibrium experiments were conducted at 23° C. and in 50 mM phosphate buffer containing 150 mM NaCl, pH 7.4. Three loading concentrations (18, 30 and 42 µM) were scanned at 230 nm, and sedimented to equilibrium at 20 krpm, 26.6 krpm, 33.3 krpm, and at 39.9 krpm, resulting in 12 scans which were globally fit to multiple models as described previously [Johnson et al., Biophys. J. 36(3): 575-588 (1981); Demeler et al., UltraScan A Comprehensive Data Analysis Software Package for Analytical Ultracentrifugation Experiments. Analytical Ultracentrifugation—Techniques and Methods. Royal Society of Chemistry: 2005]. The most appropriate model was chosen based on visual inspection of the residual run patterns and based on the best statistics. Statistics were evaluated with the Monte Carlo analysis implemented in UltraScan [Demeler et al., Colloid & Polymer Science 286(2): 129-137 (2008)].

Figure 4:
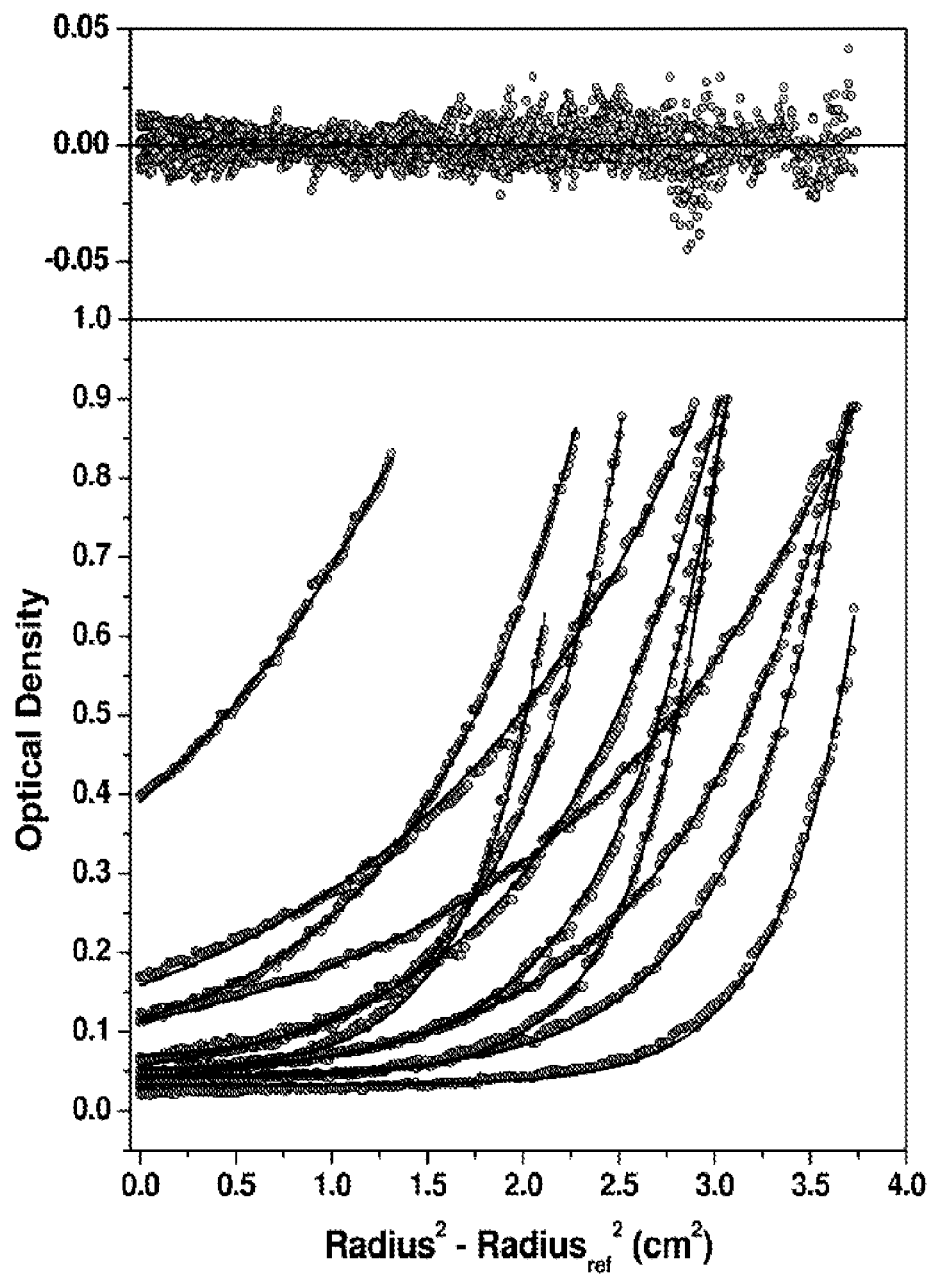
FIG. 4 shows equilibrium results for single ideal species fit of 1. The residuals are shown in the top panel and indicate random distribution. The lower panel shows the experimental data (grey circles) overlayed with traces corresponding to the fitted model (solid lines).

A good fit was obtained when all scans were fitted globally to a single ideal species model (RMSD=7.3631e-03, see FIG. 4). A fixed molecular weight distribution model with 100 molecular weight slots between 10,000 and 50,000 Dalton provided slightly better statistics (RMSD=4.6435e-03) because of the additional degrees of freedom. Both models suggested a mostly homogeneous solution with a species (single ideal species fit: 33.38 kDa, Monte Carlo analysis for the fixed molecular weight distribution statistics: weight-average molecular weight: 34.67 kDa, number-average molecular weight: 32.34 kDa, and Z-average molecular weight: 36.28 kDa). Using more degenerate models that require additional parameters (equilibrium constants or multiple components) did not improve the fit with any statistical significance.

Velocity:

Sedimentation velocity experiments were conducted in the same buffer as the equilibrium experiments. Velocity experiments were performed at 50 krpm and 23° C., scans were taken at 230 nm in intensity mode. The data were analyzed with the 2-dimensional spectrum analysis (2DSA) [Brookes et al., European Biophysics Journal 39(3): 405-414 (2010)] and time invariant noise was subtracted. 2DSA results were further refined with the genetic algorithm analysis (GA) [Brookes et al., Proceedings of the 9th annual conference on Genetic and evolutionary computation 361-368 (2007)] coupled with Monte Carlo (MC) analysis [Demeler et al., UltraScan A Comprehensive Data Analysis Software Package for Analytical Ultracentrifugation Experiments. Analytical Ultracentrifugation—Techniques and Methods. Royal Society of Chemistry: 2005]. Sedimentation coefficient distributions were calculated with the van Holde-Weischet analysis [Demeler et al., Anal. Biochem. 335(2): 279-288 (2004)].

Figure 5:
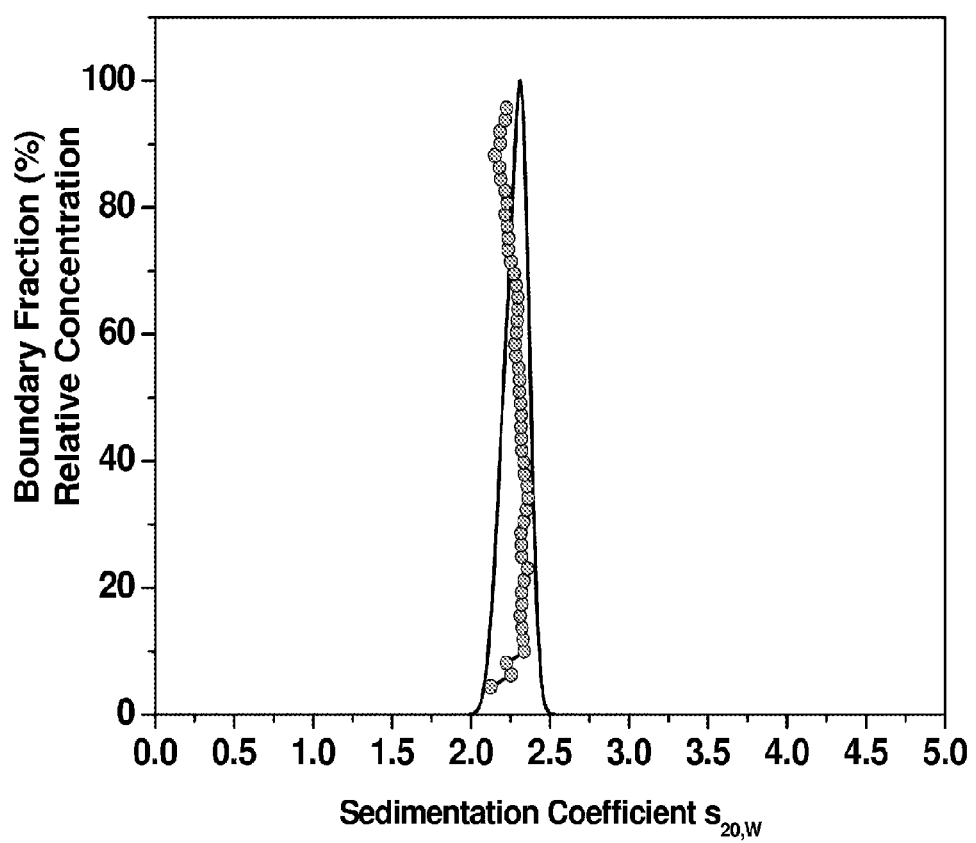
FIG. 5 shows van Holde-Weischet results for YRB109-PEG2000. Integral distribution (grey circles) and g(s) distribution (solid line) suggest presence of a single, homogeneous solute with a sedimentation coefficient of 2.28 s.

The van Holde-Weischet analysis suggested the presence of a homogeneous solution with a weight-average sedimentation coefficient of 2.28 s (FIG. 5), indicating a slight concentration dependent non-ideality. Weight-average sedimentation coefficients determined with the 2DSA-MC and the GA-MC analysis were both 2.26 s. The GA-M with 94% of the signal corresponding to a single species with molecular weight of 33.74 kDa (95% confidence intervals: 33.70, 33.78 kDa), and a frictional ratio of 1.370 (95% confidence intervals: 1.367, 1.373), suggesting moderate anisotropy.

Conclusion:

Sedimentation analysis from both equilibrium and velocity experiments suggested a strikingly similar molecular weight, differing by less than 0.2%, and suggested the presence of a single species. This molecular weight was consistent with a hexameric assembly of 1. However, literature precedents [Liu et al., Proc. Natl. Acad. Sci. U.S.A. 103(42): 15457-15462 (2006)] suggested the presence of a heptameric structure. Since both sedimentation velocity and sedimentation equilibrium experiments only measure the buoyant molecular weight of the sample, errors can be introduced when the partial specific volume is in error. The partial specific volume of 1 was not determined in an independent measurement, but it is reasonable to assume that due to the presence of the $PEG_{2000}$ chain, the partial specific volume is actually higher than was estimated. The partial specific volume was therefore also fitted using the single species ideal equilibrium model, holding the molecular weight fixed at the theoretical estimate of 39,921 Daltons and determined a partial specific volume of 0.809 ml/mg, which is reasonable considering the presence of the $PEG_{2000}$ chain. Importantly, it can be concluded that at concentrations between 18 and 42 µM 1 is present in a homogeneous composition and either as a hexamer or heptameric oligomer.

DNA (Nucleic Acids) Binding Studies

Figure 6:
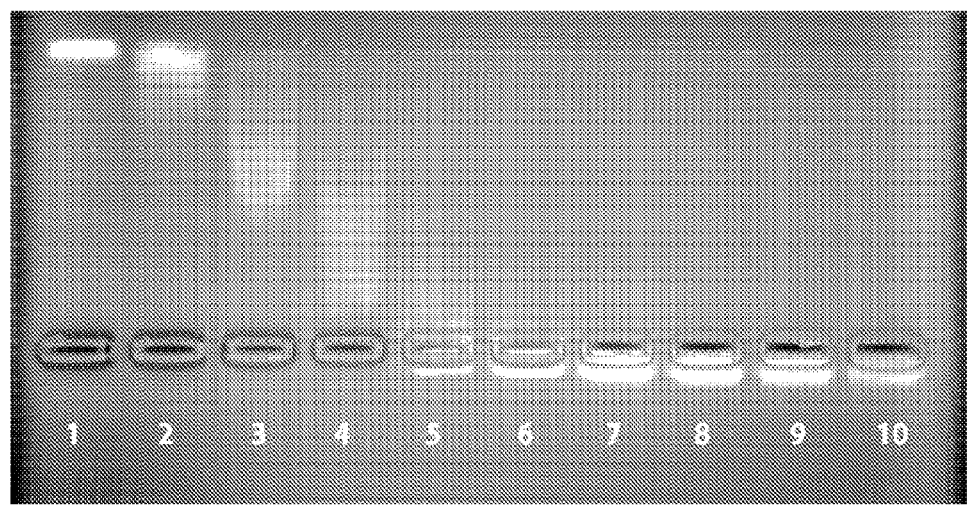
FIG. 6 depicts agarose gel electrophoresis of complexes of 2 and a 1200 bp DNA fragment. Each sample was prepared in a volume of 20 μl Well 1: 200 ng of 1200 bp DNA fragment; Well 2—10: 200 ng of 1200 bp DNA fragment+2 at a concentration of 2.5-5-7.5-10-15-20-25-35-45 μM.

The ability of compounds 1 and 2 to bind to nucleic acids was assayed by agarose gel shift assays where DNA was mixed with peptides 1 and 2 in different ratio. (FIG. 6). According to these studies at a peptide concentration of 20 µM, no free DNA can be detected in the sample. This corresponds to a ratio of approximately 1600 peptide molecules for one molecule of DNA, or 1.3 peptides per base pair.

Structural Characterization of the Complexes

Complexes between nucleic acid templates and molecules 1, 2 and 3 were prepared under conditions where no more free DNA could be detected by gel electrophoresis and analyzed by transmission electron microscopy (TEM).

Effect of the Molecular Weight of the PEG Chain

Figure 7:
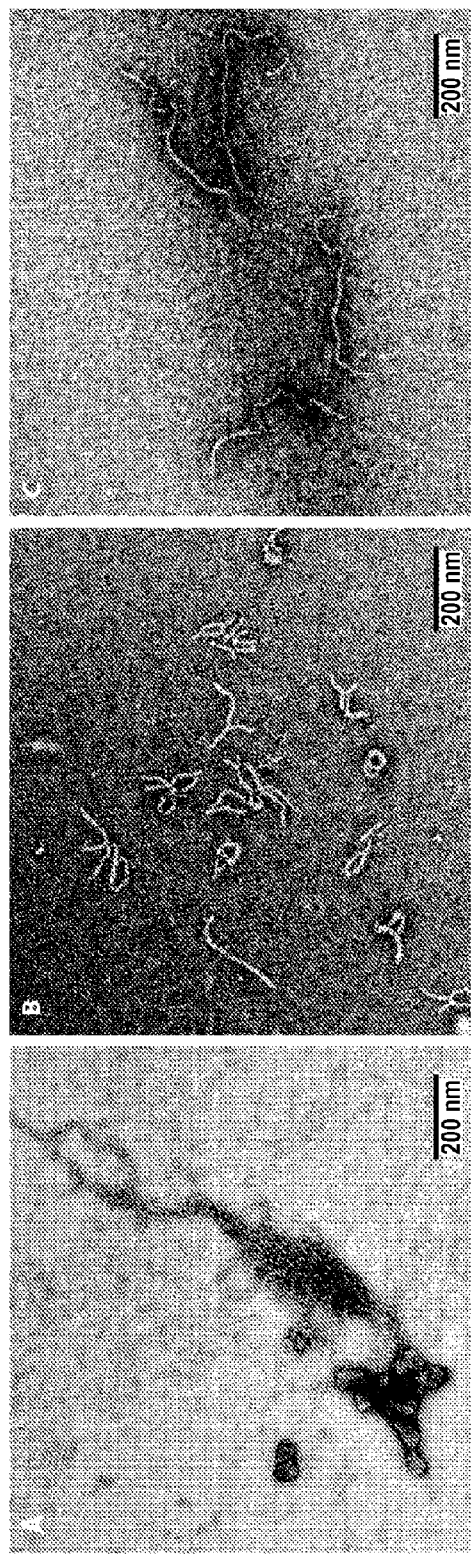
FIG. 7 shows the effect of the length of the PEG segment on the peptide-circular plasmid DNA complexes morphology. A Complex between 3 (80 μM) and plasmid pbr322 (200 ng) in 20 μl of 25 mM Tris buffer (pH 7.4, 25 mM) B Complex between 1 (80 μM) and plasmid pbr322 (200 ng) in 20 μl of 25 mM Tris buffer (pH 7.4, 25 mM) C Complex between 2 (80 μM) and plasmid pbr322 (200 ng) in 20 μl of 25 mM Tris buffer (pH 7.4, 25 mM).

The addition of a PEG chain to the DNA binding self-assembling coiled-coil peptide clearly inhibits the aggregation of the complexes into larger, less defined aggregates. FIG. 7 shows complexes between a plasmid pBR322 DNA template and the three peptides 1, 2 and 3 under identical conditions of concentration and pH.

Complexes between the plasmid PBR322 and molecule 3 yield a highly heterogenous mixture of aggregated globular and filamentous aggregates. The addition of the $PEG_{2000}$ chain on molecule 1 is clearly beneficial for the preparation of more defined complexes, as in this case individual complexes are observed. However, their morphology is heterogenous and consists in a mixture of rods, branched and toroidal complexes.

Figure 8:
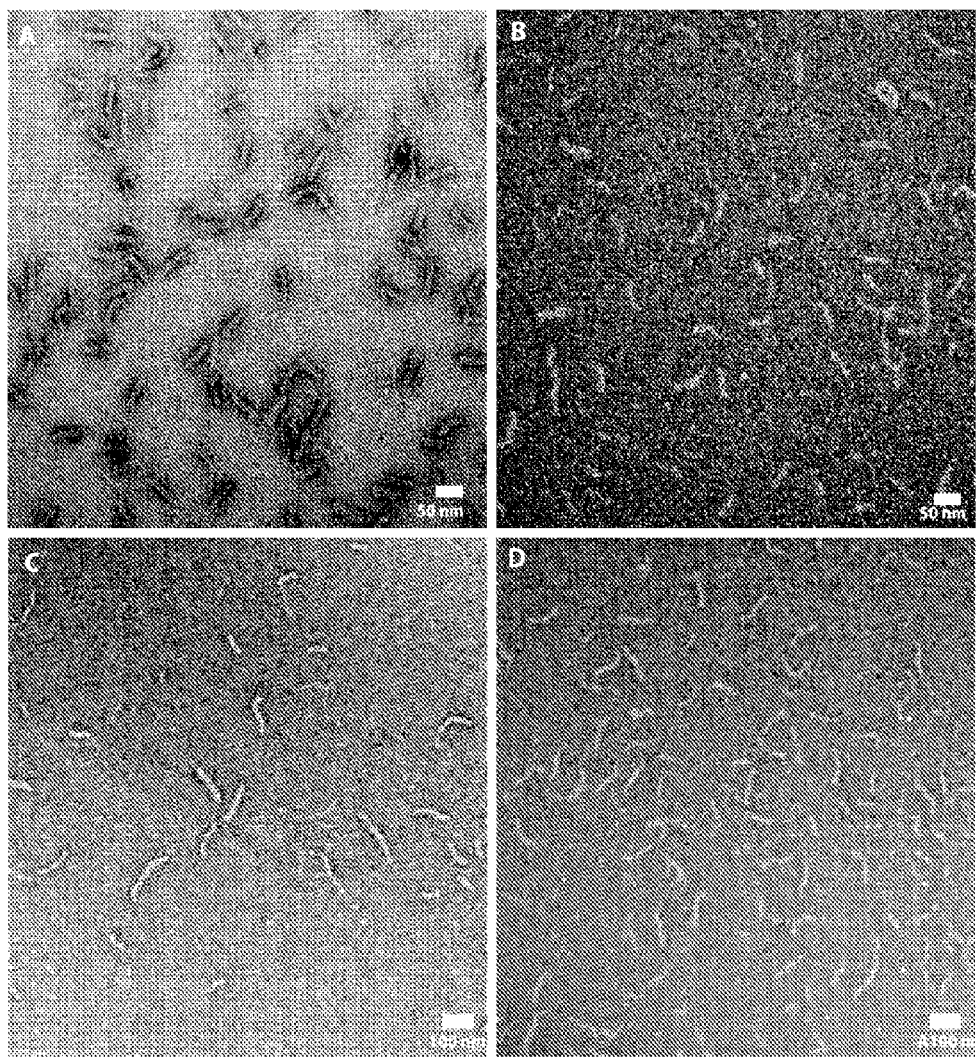
FIG. 8 shows the effect of the length of the PEG segment on the peptide-linear double strand DNA complexes morphology. A Complex between 1 (80 μM) and ds 150 bp DNA fragment (200 ng) in 20 μl of 25 mM Tris buffer (pH 7.4, 25 mM) B Complex between 2 (80 μM) and ds 150 bp fragment (200 ng) in 20 μl of 25 mM Tris buffer (pH 7.4, 25 mM) C Complex between 1 (80 μM) and ds 300 bp DNA fragment (200 ng) in 20 μl of 25 mM Tris buffer (pH 7.4, 25 mM) D Complex between 2 (80 μM) and ds 300 bp fragment (200 ng) in 20 μl of 25 mM Tris buffer (pH 7.4, 25 mM).

When the molecular weight of the PEG segment was increased to 5000 g·mol-1, a dramatic improvement in the complexes homogeneity was observed in terms of both dimension and morphology. When 2 was mixed with the same plasmid PBR322 template only filamentous complexes were observed. The toroid proportion is insignificant as they are difficult to observe. Furthermore, the length of the complexes was homogenous, and around 706 nm in average. The calculated length of the PBR322 plasmid in a supercoiled conformation is 737 nm, very close to the observed dimensions. A slight shortening of the complexes can be explained by the contraction of DNA in the presence of multivalent counterions. Complexes of short double strand DNA fragments (25-1200 bp) have also been prepared and observed by TEM. (FIG. 8). The expected control of the dimensions of the complexes by template effect clearly obeys different regimes depending both of the length of the template and design of the artificial capsomers.

For complexes between short DNA fragments and 1 and 2, the design disclosed herein was validated by the observation of negatively stained complexes having a rodlike morphology and having predominantly the length of the DNA template. (FIG. 8) As reported recently for rodlike block copolymer-DNA complexes, the length distribution of the rods is not random, and actually corresponds to a distribution of quantized lengths [Osada et al., J. Am. Chem. Soc. 132(35): 12343-12348 (2010)]. It was proposed that this discrete distribution originates from the appearance of a crushing force on the DNA rods upon binding to multivalent cations and neutralization of its backbone negative charges. The DNA molecule would then fold under the application of this compressive according to different quantized bending modes according to the Euler theory [Osada et al., J. Am. Chem. Soc. 132(35): 12343-12348 (2010)]. The different Euler bending mode can result in the folding of the initial DNA-cation rod in shorter rods having a length $l=\frac{1}{2}(n+1)$ of the plasmid DNA contour length where n is the folding number. Folding of the DNA in the complexes is due to compressive forces emerging after neutralization of the negative charges of the DNA by multivalent counterions according to the Manning theoretical model of DNA stiffness.

Figure 9:
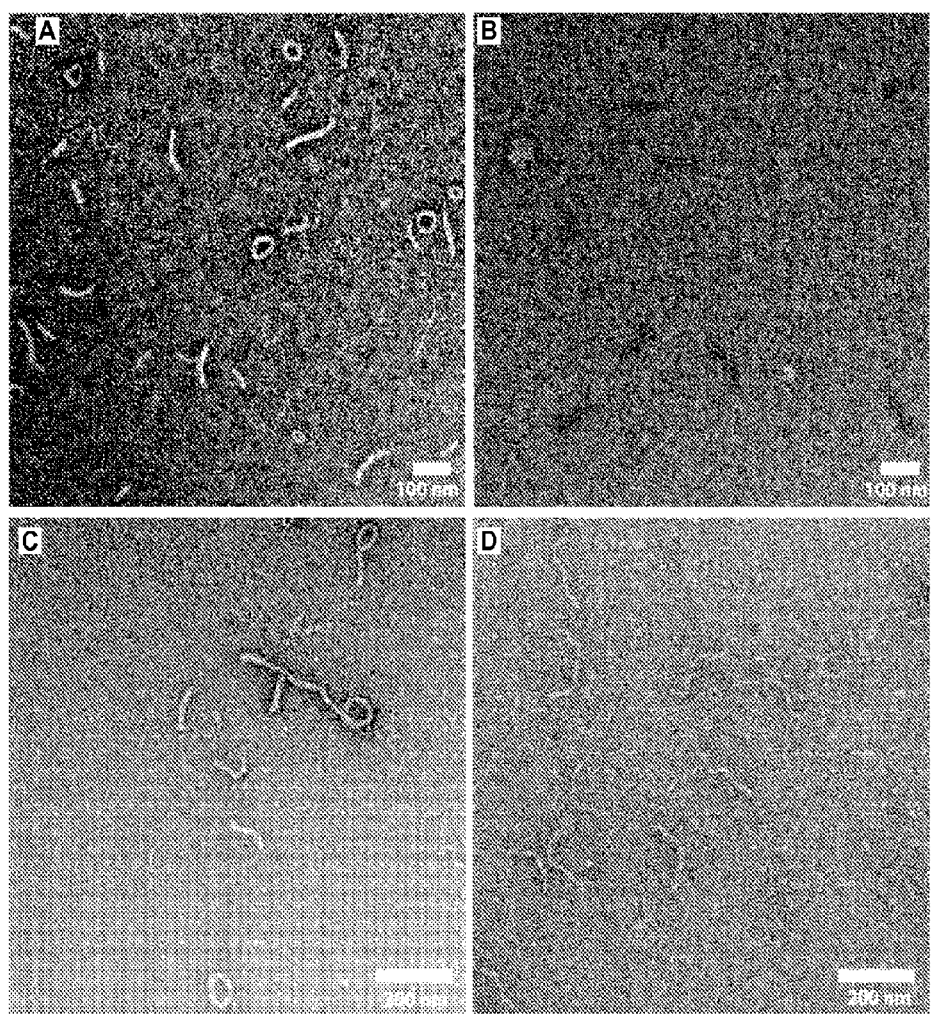
FIG. 9 shows the effect of the length of the PEG segment on the peptide-linear double strand DNA complexes morphology. A Complex between 1 (80 μM) and ds 600 bp DNA fragment (200 ng) in 20 μl of 25 mM Tris buffer (pH 7.4, 25 mM) B Complex between 2 (80 μM) and ds 600 bp fragment (200 ng) in 20 μl of 25 mM Tris buffer (pH 7.4, 25 mM) C Complex between 1 (80 μM) and ds 1200 bp DNA fragment (200 ng) in 20 μl of 25 mM Tris buffer (pH 7.4, 25 mM) D Complex between 2 (80 μM) and ds 1200 bp fragment (200 ng) in 20 μl of 25 mM Tris buffer (pH 7.4, 25 mM).

When the length of the template was increased above 300 bp, however, the morphology of the complexes between DNA fragments and 1 became more heterogenous as the length of the template increased yielding a mixture of the expected filamentous complexes of different length and toroidal complexes (FIG. 9).

The situation was different for complexes between DNA fragments and 2, as in these cases the toroid formation was effectively suppressed. Complexes prepared with 2 showed homogenous rods having predominantly a length corresponding to the DNA template folded in two. Therefore increasing the length of the PEG also affects the homogeneity of the artificial viruses. Going from a $PEG_{2000}$ to a $PEG_{5000}$ conjugate not only suppressed the toroid formation, but also favored the formation of almost monodisperse filamentous nanostructures. This effect is explained by an increase in steric repulsion between the PEG corona of the self-assembled mushrooms. This repulsion increases the rigidity of the complexes and prevents their transition into shorter rods or toroids by counterbalancing the natural tendency of the neutralized DNA the complexes core to bend and fold into rods or condense into toroids.

Figure 10:
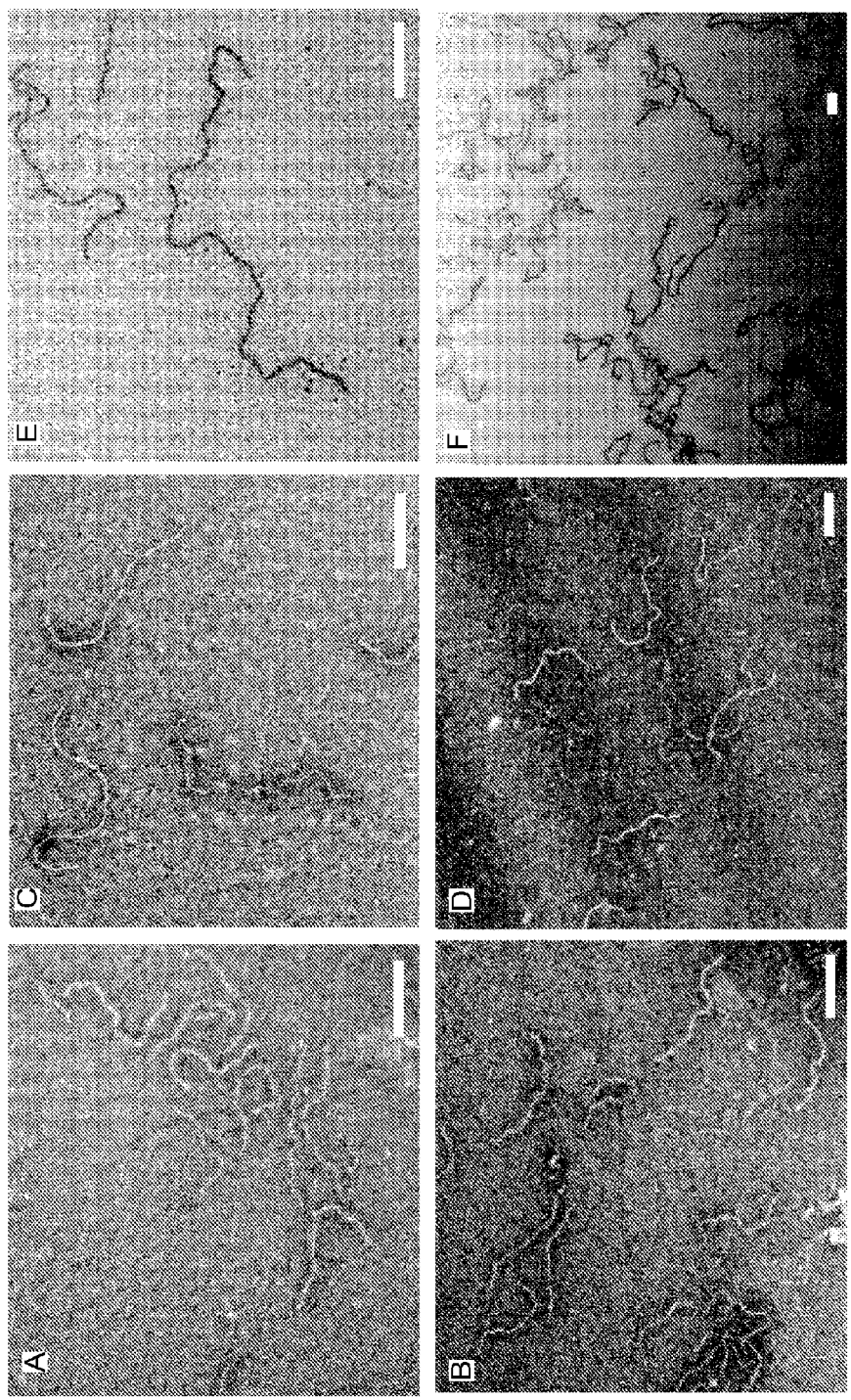
FIG. 10 depicts the effect of the size of the plasmid DNA template on the peptide/DNA complexes length. A Complex between 2 (80 μM) and puC19 plasmid (200 ng, 2686 bp) in 20 μl of 25 mM Tris buffer (pH 7.4, 25 mM) B Complex between 2 (80 μM) and puC19 plasmid (200 ng, 2686 bp) in 20 μl of 25 mM Tris buffer (pH 7.4, 25 mM) C Complex between 2 (80 μM) and pbr322 plasmid (200 ng, 4361 bp) in 20 μl of 25 mM Tris buffer (pH 7.4, 25 mM) D Complex between 2 (80 μM) and pbr322 plasmid (200 ng, 4361 bp) in 20 μl of 25 mM Tris buffer (pH 7.4, 25 mM) E Complex between 2 (80 μM) and pKLAC1-malE plasmid (200 ng, 10153 bp) in 20 μl of 25 mM Tris buffer (pH 7.4, 25 mM) F Complex between 2 (80 μM) and pKLAC1-malE plasmid (200 ng, 10153 bp) in 20 μl of 25 mM Tris buffer (pH 7.4, 25 mM). Scale bar 200 nm for all images.

In the case of plasmid DNA templates, the observed length of the complexes corresponds to the length of the template in a supercoiled conformation, indicating no folding in this case. The length of the complexes was also controlled by changing the size of the plasmid DNA used as templates (FIG. 10).

The toroid formation was also practically suppressed, as these circular structures were present in insignificant amounts for samples equilibrated for a few hours. The toroid proportion does not increase over time, as samples equilibrated for more than a week are still homogenous. Therefore the methods described herein allow for the control of both the morphology and dimensions of the DNA-peptides complexes.

Because highly homogenous complexes were obtained, this strategy provides for the precise optimization of the morphology and dimensions of these artificial viruses. In the context of cancer therapy, being able to control the length of the nanostructures described herein allows one to take advantage of the enhanced permeability and retention (EPR) effect [Maeda et al., Bioconjugate Chem. 21(5): 797-802 (2010)] and optimize the dimension of the nanostructures [Gratton et al., Proc. Natl. Acad. Sci. U.S.A. 105(33): 11613-11618 (2008)] to achieve efficient endocytosis of the artificial vectors once their diffusion into tumors has occurred.

The invention described in the examples above serves only to illustrate the disclosure and is not intended to limit the scope of the disclosure in any way.

All documents cited herein are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

What is claimed is:

1. A peptide segment comprising a first domain, a second domain and a third domain, wherein:
   (a) the first domain is selected from the group consisting of spermine, oligoethyleneimine, polyethyleneimine, protamine, and a histone, and is positioned at a first terminus of the second domain;
   (b) the second domain comprises an amino acid sequence of SEQ ID NO: 1, and is positioned between the first domain and the third domain; and
   (c) the third domain is a polyethylene glycol (PEG), and is positioned at a second terminus of the second domain,
   wherein a plurality of peptide segments have the ability to self assemble to form a capsomer.

2. The peptide segment of claim 1, comprising at least one non-naturally occurring amino acid.

3. The peptide segment of claim 1, wherein the PEG has an average molecular weight of about 2 kilodaltons to about 100 kilodaltons.

4. The peptide segment of claim 1, wherein the PEG has an average molecular weight of about 2 kilodaltons to about 5 kilodaltons.

5. A capsomer comprising a plurality of peptide segments, each according to claim 1, wherein the capsomer is formed by the self-assembly of the plurality of peptide segments, and wherein a plurality of capsomers have the ability to self assemble to form a nanostructure.

6. A nanostructure comprising a plurality of capsomers, each capsomer according to claim 5, and further comprising a charged compound.

7. The nanostructure of claim 6, comprising at least two different charged compounds.

8. The nanostructure of claim 6, wherein each capsomer is identical.

9. The nanostructure of claim 6, comprising at least two capsomers that are not identical.

10. The nanostructure of claim 6, wherein the charged compound is a nucleic acid.

11. The nanostructure of claim 10, wherein the nucleic acid is double stranded.

12. The nanostructure of claim 6, wherein the charged compound is encapsulated by the plurality of capsomers.

13. The nanostructure of claim 6, which has an electronic property selected from the group consisting of semiconductivity, conductivity and electrochromism.

14. The nanostructure of claim 6, which is a monodisperse filamentous structure.

* * * * *

SEQUENCE LISTING

<160> NUMBER OF SEQ ID NOS: 1

<210> SEQ ID NO 1
<211> LENGTH: 34
<212> TYPE: PRT
<213> ORGANISM: Artificial sequence
<220> FEATURE:
<223> OTHER INFORMATION: Synthetic polypeptide

<400> SEQUENCE: 1

```
Arg Glu Gly Val Ala Lys Ala Leu Arg Ala Val Ala Asn Ala Leu His
1               5                   10                  15

Tyr Asn Ala Ser Ala Leu Glu Glu Val Ala Asp Ala Leu Gln Lys Val
            20                  25                  30

Lys Met
```